(12) United States Patent
Carolo

(10) Patent No.: US 6,512,167 B1
(45) Date of Patent: *Jan. 28, 2003

(54) HYBRID MAIZE SEED AND PLANT RPG824

(75) Inventor: Pierre Carolo, Vendôme (FR)

(73) Assignee: Rustica Prograin Genetique, Mondonville (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/498,611

(22) Filed: Feb. 4, 2000

(51) Int. Cl.⁷ .............................. A01H 5/00; A01H 5/10; A01H 1/00; A01H 1/02; C12N 5/04
(52) U.S. Cl. .................... 800/320.1; 800/265; 800/266; 800/268; 800/271; 800/275; 800/278; 435/412; 435/421; 435/424; 435/430; 435/430.1; 435/468
(58) Field of Search ............................... 800/320.1, 298, 800/275, 268, 266, 271, 278, 265; 435/412, 424, 430, 430.1, 421, 468

(56) References Cited

U.S. PATENT DOCUMENTS 6,043,418 A * 3/2000 Johnson .................... 800/320.1

OTHER PUBLICATIONS

Principles of Plant Breeding, p. 156.*
Phillips et al, Cell/Tissue Culture and In Vitro Manipulation, p. 358, section 5–2.*

* cited by examiner

Primary Examiner—David T. Fox
(74) Attorney, Agent, or Firm—Patterson, Thuente, Skaar & Christensen, P.A.

(57) ABSTRACT

A maize hybrid designated RPG824, the plants and seeds of maize hybrid RPG824, methods for producing a maize plant, either inbred or hybrid, produced by crossing the maize hybrid RPG824 with itself, with another maize plant, or transforming said maize hybrid.

40 Claims, No Drawings

HYBRID MAIZE SEED AND PLANT RPG824

FIELD OF THE INVENTION

This invention relates to maize improvement. More specifically, this invention relates to a hybrid maize variety designated RPG824.

BACKGROUND OF THE INVENTION

Maize

Maize or corn (*Zea mays* L.) is one of the major annual crop species grown for grain and forage. A monocot, maize is a member of the grass family (Gramineae) and bears seeds in female inflorescences (usually called ears) and pollen in separate male inflorescences (usually called tassels).

In the U.S., maize is almost exclusively produced by growing hybrid varieties (cultivars). Maize hybrids are typically produced by seed companies and sold to farmers. On farms, maize hybrids are usually grown as a row crop. During the growing season herbicides are widely used to control weeds; fertilizers are used to maximize yields; and fungicides and insecticides are often used to control disease pathogens and insect pests. Before maturity, maize plants may be chopped and placed in storage where the chopped forage (stover) undergoes fermentation to become silage for livestock feed. At maturity in the fall, the seeds are harvested as grain. The grain may be directly fed to livestock or transported to storage facilities. From storage facilities, the grain is transported to be used in making an extremely large number of products, including food ingredients, snacks, pharmaceuticals, sweeteners, and paper products (see, e.g., S. A. Watson and P. E. Ramstad, Eds., Corn: Chemistry and Technology, American Association of Cereal Chemists, Inc., St. Paul, Minn. (1987)).

While the agronomic performance of maize hybrids has improved, there is a continuing need to develop better hybrids with increased and more dependable grain and stover yields. Moreover, heat and drought stress and continually changing insect predators and disease pathogens present hazards to farmers as they grow maize hybrids. Thus, there is a continual need for maize hybrids which offer higher grain yields in the presence of heat, drought, pathogens and insects.

Inbred Lines and Hybrid Varieties

The ultimate purpose for developing maize inbred lines is to be able to dependably produce hybrids. Commercially viable maize hybrids, like hybrids in many other crop species, manifest heterosis or hybrid vigor for most economically important traits.

Plants resulting from self-pollination (or from other forms of inbreeding) for several generations are termed inbreds (inbred lines). These inbreds are homozygous at almost all loci. When self-pollinated, these inbreds produce a genetically uniform population of true breeding inbred progeny. These inbred progeny possess genotypes and phenotypes essentially identical to that of their inbred parent. A cross between two different inbreds produces a genetically uniform population of hybrid $F_1$ plants. These $F_1$ plants are genetically uniform, but are highly heterozygous. Progeny from a cross between two hybrid $F_1$ plants are also highly heterozygous, but are not genetically uniform.

One important result of this phenomenon is that seed supplies of an inbred may be increased by self-pollinating the inbred plants. Equivalently, seed supplies of the inbred may be increased by growing inbred plants such that only pollen from these inbred plants is present during flowering (anthesis), e.g., in spaced or timed isolation. Seed arising from inbred parents successfully grown in isolation is genetically identical to the inbred parents. Another important result is that hybrids of inbred lines always have the same appearance and uniformity and can be produced by crossing the same set of inbreds whenever desired. This is because inbreds, themselves, are genetically uniform. Thus, a hybrid created by crossing a defined set of inbreds will always be the same. Moreover, once the inbreds giving rise to a superior hybrid are identified, a continual supply of the hybrid seed can be produced by crossing these identified inbred parents.

Types of hybrids include single-cross, three-way, and double-cross. Single-cross hybrids are the $F_1$ progeny of a cross between two inbred lines (inbreds), e.g., A×B, in which A and B are inbreds. Three-way hybrids are the first generation progeny of a cross between a single-cross hybrid and an inbred, e.g., (A×B)×C, in which A×B is a single-cross hybrid of inbreds A and B and C is another inbred. Double-cross hybrids are the first generation progeny of a cross between two single-cross hybrids, e.g., (A×B)×(C×D), in which A×B and C×D are single-cross hybrids of inbreds A and B and C and D, respectively. In the U.S., single-cross hybrids currently occupy the largest proportion of the acreage used in maize production. As will be shown below, maize inbreds are assemblages of true breeding, homozygous, substantially identical (homogeneous) individuals. Single-cross hybrids are both homogeneous and highly heterozygous and are not true breeding. Three-way and double-cross hybrids are less homogeneous, but are nonetheless highly heterozygous and not true breeding as well. Hence, the only way of improving hybrids is improving component inbreds thereof. Improving maize inbreds involves procedures and concepts developed from the discipline of plant breeding.

Plant Breeding

Developing improved maize hybrids requires the development of improved maize inbreds. Maize breeding programs typically combine the genetic backgrounds from two or more inbred lines or various other broad based germplasm sources into breeding populations from which new inbred lines are developed by self-pollination (or other forms of inbreeding) and selection for desired phenotypes. The newly developed inbreds are crossed to other inbred tester lines and the hybrids from these tester crosses are then evaluated to determine whether these hybrids might have commercial potential. Thus, the invention of a new maize variety requires a number of steps. As a nonlimiting illustration, these steps may include:

(1) selecting plants for initial crosses;
(2) crossing the selected plants in a mating scheme to generate $F_1$ progeny;
(3) self-pollinating the $F_1$ progeny to generate segregating $F_2$ progeny;
(4) sequentially self-pollinating and selecting progeny from the $F_2$ plants for several generations to produce a series of newly developed inbreds which breed true and are highly uniform, yet which differ from each other;
(5) crossing the newly developed inbred lines with other unrelated inbred lines (testers) to produce hybrid seed; and
(6) evaluating the tester hybrids in replicated and unreplicated performance trials to determine their commercial value.

Plants are selected from germplasm pools to improve hybrid traits such as grain and stover yield, resistance or tolerance to diseases, insects, heat and drought, stalk quality, ear retention, and end use qualities. The plants from the germplasm pools are then crossed to produce $F_1$ plants and the $F_1$ plants are self-pollinated to generate populations of $F_2$ plants. Self-pollination and selection in $F_2$ plants and subsequent generations are illustrated below in a nonlimiting example of a pedigree method of breeding.

In the nursery, $F_2$ plants are self-pollinated and selected for stalk quality, reaction to diseases and insects, and other traits which are visually scored. During the next growing season, seeds from each selected self-pollinated $F_2$ plant are planted in a row and grown as $F_2$-derived, $F_3$ families. Selection and self-pollination is practiced among and within these $F_3$ families. In a subsequent growing season, seeds from each selected $F_3$ plant are planted in a row and grown as $F_3$-derived, $F_4$ families. Selection and self-pollination are again practiced among and within these $F_4$ families. In a subsequent growing season, seeds from each selected $F_4$ plant are planted in a row and grown as $F_4$-derived, $F_5$ families. At this point, selection is practiced predominantly among families, rather than within families, because plants within families tend to be uniform and are approaching homozygosity and homogeneity. Seeds from selected $F_5$ plants are harvested to be further selected for uniformity prior to being increased.

Simultaneous with self-pollination and selection, seeds from each selected $F_3$, $F_4$, and $F_5$ plant are planted in a female row in one or more isolation blocks along with rows planted with seed of a tester (male) inbred. These isolation blocks are often grown at winter locations so the seed harvested therefrom can be grown in performance trials during the next growing season. Prior to anthesis, tassels from the selected $F_3$, $F_4$, and $F_5$ female plants are removed before they shed pollen so that the only pollen present in the isolation block is from the tester inbred. Seeds arising from the selected $F_3$, $F_4$, and $F_5$ female plants are hybrid seeds having the selected $F_3$, $F_4$, and $F_5$ plants as maternal (seed) parents and the tester inbred as the paternal (pollen) parent.

Hybrid seeds from the isolation blocks, check hybrids, and commercially significant hybrids of the same maturity are grown in replicated performance trials at a series of locations. Each check hybrid is the result of crossing the tester parent and an inbred parent of known maturity and proven agronomic value. During the growing season, the hybrids are visually scored for any of the above-described traits. At maturity, plots in these trials are usually scored for the percentage of plants with broken or tilted stalks and dropped ears. At harvest, grain yield, grain moisture, and grain test weight are determined. The resulting data from these performance trials are analyzed and means and statistics are calculated. These statistics provide indications of the reliability (precision) of the means obtained from the performance trials. Means from these performance trials are then used to further cull plants in the nursery on the basis of unsatisfactory performance of their hybrids. Performance trials for earlier generations typically evaluate more hybrids and are planted at fewer locations than performance trials for later generations.

At some point, seed supplies of elite inbred candidates from the nursery are increased and are used to produce larger amounts of experimental hybrids. These experimental hybrids are evaluated in replicated performance trials at maximum possible numbers of locations and may be grown alongside commercial hybrids from other seed companies in farmer fields in unreplicated trials as well. If the experimental hybrids perform well with respect to the commercial hybrids in these replicated and unreplicated trials, they are commercialized.

While the above-described pedigree method is widely used to develop maize inbreds, variations are widely used as well. Moreover, other breeding method protocols such as those for bulks, backcrossing, recurrent selection, and mass selection may be practiced in addition to, or in lieu of, the pedigree method described above. Theories and exemplary protocols for the pedigree method, bulk method, recurrent selection, and mass selection are known to the art, but are disclosed in, e.g., A. R. Hallauer and J. B. Miranda Fo, Quantitative Genetics in Maize Breeding, Iowa State University Press, Ames, Iowa (1981); G. Namkoong, Introduction to Quantitative Genetics in Forestry, U.S. Dept. Agric. Forest Service Tech. Bull. No. 1588 (1979); F. N. Briggs and P. F. Knowles, Introduction to Plant Breeding, Reinhold Publishing Company, New York (1967); R. W. Allard, Principles of Plant Breeding, Wiley and Sons, New York (1960); N. W. Simmonds, Principles of Crop Improvement, Longman Group, Ltd., London (1979); and J. M. Poehlman, Breeding Field Crops, 2d Ed., AVI Publishing Co., Inc. Westport, Conn. (1979), the relevant disclosures of each hereby incorporated by reference.

As discussed above, hybrids of promising advanced breeding lines are thoroughly tested and compared to appropriate check hybrids in environments representative of the commercial target area(s), usually for 2–3 years. The best hybrids identified by these performance trials are candidates for commercial exploitation. Seed of each of the newly developed inbred parents of these hybrids is further purified by eliminating off types and increased in steps leading to commercial production. These prerequisite activities to marketing newly developed hybrids usually take from eight to 12 years from the time the first breeding cross is made. Therefore, development of new cultivars is a time-consuming process requiring precise planning and efficient allocation and utilization of limited resources.

Identification of genetically superior individuals is one of the most challenging issues confronting the plant breeder. For many economically important traits, the true genotypic expression of the trait is masked by effects of other (confounding) plant traits and environmental factors. One method of identifying a superior hybrid is to observe its performance relative to other experimental hybrids and to a series of widely grown standard cultivars. However, because a single observation is usually inconclusive, replicated observations over a series of environments are necessary to provide an estimate of the genetic worth of a hybrid.

Maize is an important and valuable field crop. Hence, a continuing goal of plant breeders is to develop high-yielding maize hybrids which are otherwise agronomically desirable and which are produced by stable inbred lines. To accomplish this goal, the maize breeder must continually develop superior inbred parent lines. Developing superior inbred parent lines requires identification and selection of genetically unique, superior individuals from within segregating populations.

Each segregating population is the result of a combination of a multitude of genetic crossover events, independent assortment of specific combinations of alleles at many gene loci, and inheritance of large groups of genes together due to the effects of linkage. Thus, the probability of selecting any single individual with a specific superior genotype from a breeding cross is infinitesimally small due to the large number of segregating genes and the virtually unlimited recombinations of these genes. Nonetheless, the genetic variation present among the segregating progeny of a breeding cross enables the identification of rare and valuable new genotypes. These rare and valuable new genotypes are neither predictable nor incremental in value, but are rather the result of expressed genetic variation. Thus, even if the genotypes of the parents of the breeding cross can be completely characterized and a desired genotype known, only a few, if any, individuals with the desired genotype may be found within a large, segregating $F_2$ population. Typically, however, neither the genotypes of the parents used in the breeding cross nor the desired progeny genotype to be selected are known to any extent.

In addition to the preceding problem, it is not known with any degree of certainty how the new genotype would interact with the environment. This uncertainty is measured statistically by genotype-by-environment interactions and is an important, yet unpredictable, factor in plant breeding. A breeder of ordinary skill in the art can neither predict nor characterize a priori a new desirable genotype, how the genotype will interact with various climatic factors, or the resulting phenotypes of the developing lines, except perhaps in a very broad and gross fashion. Moreover, a breeder of ordinary skill in the art would also be unable to re-create the same line twice from the very same original parents because the breeder is unable to direct how the parental genomes will combine in the progeny or how the resulting progeny will interact with environmental conditions when undergoing selection. This unpredictability results in the expenditure of large amounts of limited research resources to develop each superior new maize inbred line.

A reliable method of controlling male fertility (pollen viability) in plants provides means for efficient and economical subsequent hybrid production. This is also the case when plant breeders are developing maize hybrids in breeding programs. All breeding programs rely on some sort of system or method of pollen control and there are several methods of pollen control available to breeders. These pollen control methods include barriers such as bags for covering silks and collecting pollen from individual plants, manual or mechanical emasculation (detasseling), cytoplasmic male-sterility (CMS), genetic male-sterility, and gametocides.

Hybrid maize seed is usually produced commercially by using a male-sterility system, manual or mechanical detasseling, or a combination of both. In typical commercial hybrid seed production, alternate strips of two maize inbreds are planted in a field. The tassels are removed from the inbred designated to be the seed or female parent. Alternatively, the female is male-sterile and is not detasseled. If there is sufficient isolation from sources of foreign maize pollen, the ears of the female inbred will be fertilized only with pollen from the other (male) inbred. The resulting seed, harvested from the female parents in a successful hybrid production effort, is hybrid $F_1$ seed which will germinate and grow into hybrid $F_1$ plants.

Manual or mechanical detasseling can be avoided by using inbreds with cytoplasmic male-sterility (CMS). CMS requires both a homozygous nuclear locus and the presence of a cytoplasmic factor for sterility, otherwise the plant will produce viable pollen. The CMS system requires A-lines (females), B-lines (maintainers), and R-lines (males). Male-sterile A-lines are homozygous for a nuclear allele for pollen sterility and possess the cytoplasmic factor for pollen sterility as well. B-lines produce viable pollen because they are homozygous for the sterile nuclear allele but possess a fertile cytoplasmic factor. With the exception of the allele for pollen fertility, B-lines usually have a nuclear genome essentially identical to that of their complimentary A-line. R-lines are homozygous for a nuclear allele for fertility and possess a fertile cytoplasmic factor. Thus, R-lines produce viable pollen. Seed of male-sterile A-lines is increased by being pollinated by complimentary B-lines. The resulting seed grows into male-sterile A-line plants because the fertile cytoplasmic factor from the B-lines is not transmitted by B-line pollen. Hybrid seed is produced by pollinating A-line plants with pollen from R-line plants. The resulting hybrid seed is heterozygous at the nuclear locus and possesses the sterile cytoplasmic factor. Thus, the hybrid seed will grow into plants which produce viable pollen.

In addition to CMS, there are several methods conferring genetic male-sterility. One method involves multiple loci (including a marker gene in one case) which confer male-sterility, as disclosed in U.S. Pat. Nos. 4,654,465 and 4,727,219 to Brar et al. Another method disclosed by U.S. Pat. Nos. 3,861,709 and 3,710,511 to Patterson uses chromosomal reciprocal translocations, deficiencies, and duplications. These and all patents referred to are hereby incorporated by reference. In addition to these methods, U.S. Pat. No. 5,432,068 to Albertsen et al., describes a system of induced nuclear male-sterility which includes: identifying a gene critical to male fertility; "silencing" this critical gene; replacing the native promoter from the critical gene with an inducible promoter; and inserting the genetically engineered gene back into the plant. The resulting plant is male-sterile while the inducible promoter is not operative because the male fertility gene is not transcribed. Fertility is restored by inducing the promoter with a non-phytotoxic chemical which induces expression of the critical gene, thereby causing the gene conferring male fertility to be transcribed. U.S. Pat. Nos. 5,689,049 and 5,689,051 to Cigan et al. discloses a transgenic maize plant rendered male-sterile by being transformed with a genetic construct including regulatory elements and DNA sequences capable of acting in a fashion to inhibit pollen formation or function.

Yet another male-sterility system delivers a gene encoding a cytotoxic substance into the plant. The cytotoxic substance is associated with a male tissue-specific promoter or an antisense system. In each instance, a gene critical to fertility is identified and an antisense transcription to that gene is inserted in the plant (See e.g., Fabinjanski, et al., EPO 89/3010153.8 Publication No. 329,308 and PCT Application No. PCT/CA90/00037 published as WO 90/08828).

Another system potentially useful to confer male-sterility uses gametocides. Gametocides are topically applied chemicals affecting the growth and development of cells critical to male fertility. Application of gametocides affects fertility in the plants only for the growing season in which the gametocide is applied. See, e.g., U.S. Pat. No. 4,936,904 to Carlson (N-alkyl-2-aryl-4-oxonicotinates, N-alkyl-5-aryl-4-oxonicotinates, N-alkyl-6-aryl-4-oxonicotinates, N-alkyl-2,6-diaryl-4-oxonicotinates). However, inbred genotypes differ in the extent to which they are rendered male-sterile by gametocides and in the growth stages at which the gametocides must be applied.

During hybrid seed production, incomplete detasseling or incomplete inactivation of pollen from the female parent will cause some of the female parent plants to be self-pollinated. These selfed female plants will produce seed of the female inbred, rather than the desired hybrid seed. The selfed seed of the female plants will then be harvested and packaged along with the hybrid seed. Alternatively, seed from the male inbred line may also be present among hybrid seed if the male plants are not eliminated after pollination. In either case, once the mixture of hybrid and "selfed" seed is planted it is possible to identify and select the female or male inbreds growing among hybrid plants. Typically these "selfs" are easily identified and selected because of their decreased vigor for vegetative and/or reproductive characteristics (e.g., shorter plant height, small ear size, ear and kernel shape, or cob color). Identification of these selfs can also be accomplished through molecular marker analyses. See, e.g., Smith et al., "The Identification of Female Selfs in Hybrid Maize: A Comparison Using Electrophoresis and Morphology", Seed Science and Technology 14:1–8 (1995), the disclosure of which is hereby incorporated by reference. Through these technologies, the homozygosity of the self-pollinated line can be verified by analyzing allelic composition at various loci along the genome. These methods allow for rapid identification of the invention disclosed herein. See also, Sarca et al., "Identification of Atypical Plants in Hybrid Maize Seed by Postcontrol and Electrophoresis," Probleme de Genetica Teoritica si Aplicata Vol. 20(1): 29–42. Thus, this invention is contemplated to include processes in which parent inbred lines are identified and self-pollinated from within an assemblage of plants of maize hybrid RPG824.

SUMMARY OF THE INVENTION

There is provided a seed of a maize hybrid designated RPG824, a regenerable cell arising from the seed, a tissue culture arising from the regenerable cell, and a maize plant arising from the tissue culture. There is also provided a plant arising from said seed and pollen, ovules, and regenerable cells arising from the plant.

There is further provided a process of producing a maize seed, the process including identifying an inbred maize plant arising from said seed and disposed within an assemblage of hybrid maize plants of this invention and pollinating the inbred maize plant such that the maize seed arises therefrom. Pollinating may include self-pollinating and cross-pollinating.

There is yet further provided a process of sequentially inbreeding a maize plant, the process including inbreeding the hybrid maize plant of this invention and progeny thereof. The process may further include planting the seed such that maize plants arise from the seed; inbreeding the maize plants such that seed arises from the maize plants; and harvesting the seed arising from inbreeding the maize plants. Planting, inbreeding, and harvesting may be cyclically continued until a family obtained from a plant arising therefrom is substantially homogeneous.

There is still further provided a process of developing a derived maize plant. The process may include providing a maize plant arising from the seed of the present invention and introgressing a trait into the maize plant. Introgressing may include backcrossing, a tissue culture protocol inducing heritable somaclonal variation, and a transformation protocol. The transformation protocol may include microprojectile-mediated transformation, Agrobacterium-mediated transformation, electroporation, needle-like body-facilitated transformation, and any combination thereof.

According to the invention, there is provided a novel maize hybrid, designated RPG824. This invention thus relates to the seeds of maize hybrid RPG824, to the plants of maize hybrid RPG824, to methods for producing said hybrid seeds and hybrid plants. This invention also provides methods for producing other maize hybrids from maize hybrid RPG824 and to the maize hybrids derived by the use of those methods. This invention further provides hybrid maize seeds and plants produced by crossing maize hybrid RPG824 with another maize line.

DETAILED DESCRIPTION OF THE INVENTION

Maize hybrid RPG824 is well suited for growth where a moderately early maize hybrid is desired. Maize hybrid RPG824 is an $F_1$ hybrid of inbreds RPK7250 (ATCC Accession No. PTA-4730) and RPK7346 (ATCC Accession No. PTA-4731). RPK7250 and RPK7346 are described in co-pending patent applications and are assigned to the assignee of this invention. Maize hybrid RPG824 has consistently produced high grain and stover yields over a diverse array of environments. In several replicated trials, maize hybrid RPG824 has shown a grain yield advantage of about 10% when compared to elite check maize hybrids. The unexpected combination of high grain and stover yields of maize hybrid RPG824 are documented in the examples below.

Phenotypically, maize hybrid RPG824 is considered to be a tall hybrid with an accompanying high ear height. The plant height of maize hybrid RPG824 is often about 15 cm higher than other comparable check hybrids. The ear placement of maize hybrid RPG824 is often higher as well (ca. 15 cm). The highest ear of maize hybrid RPG824 usually inserts approximately at the stalk midpoint.

The early vigor of maize hybrid RPG824 is considered to be very good. Maize hybrid RPG824 typically flowers about 2 days earlier than the hybrid Anjou 285 and about 2 days later than the hybrid Fanion. During flowering, the silks of protogynous maize hybrid RPG824 usually emerge about 2 days before pollen shed.

The relative maturity of maize hybrid RPG824 is about 88RM. In France, maize hybrid RPG824 is considered to be in the C1 maturity group for grain and the S1 group for silage or FAO 240 for grain and FAO 280 for silage. In Germany, maize hybrid RPG824 is considered to be FAO 230 for grain and FAO 240 for silage.

Maize hybrid RPG824 plants typically show excellent health, manifested by superior stay-green ratings at grain physiological maturity. Maize hybrid RPG824 is considered to have medium resistance to root lodging at anthesis and good resistance to Fusarium stalk rot (*Fusarium moniliforme*) at the growth stage coinciding with physiological grain maturity. Maize hybrid RPG824 is further considered to exhibit medium tolerance to the European Corn Borer (*Ostrinia nubilalis*). Without wishing to be limited by any specific theory, it is believed that the high grain and stover yields of maize hybrid RPG824 are due, at least in part, to the unexpectedly long and indeterminate ears thereof. Indeterminate ears have the potential to increase in length in response to favorable growth conditions such as high soil fertility and abundant soil water, thereby responding with enhanced grain yields.

At low plant densities, maize hybrid RPG824 exhibits a two-ear tendency. Ears of maize hybrid RPG824 typically have 2–4 more seed rows (16–18 seed rows per cob) than many other hybrids. Moreover, the seed rows within maize hybrid RPG824 ears may contain more kernels (2–6) than other observed hybrids as well. Ears of maize hybrid RPG824 are usually covered with a fairly low number of comparatively thin husk leaves. Lengths of these husk leaves are usually sufficiently long to cover the ear to the ear tip, but usually do not extend appreciably therebeyond. The shanks, extending between stalks and ears, are considered short.

Silks of maize hybrid RPG824 exhibit a low level of anthocyanin pigmentation just after emergence, but later develop a fairly intense red pigmentation. Stalk anthocyanin pigmentation is considered to be slight (red braun). One level of brace roots of maize hybrid RPG824 is usually present. The brace roots of this invention exhibit anthocyanin pigmentation.

Tassels of maize hybrid RPG824 are considered to be medium in size, often about 8 cm in length, and bear few (6–8) semi-erect branches.

Maize hybrid RPG824 often develops one more leaf above the ear than most other maize hybrids. The leaves of maize hybrid RPG824 are considered to be long and wide.

In one instance, leaves of maize hybrid RPG824 were 10 cm in width, as compared to widths of between 8 and 9 cm for other hybrids. The leaf color of maize hybrid RPG824 is considered to be dark green. These leaves display a semi-erect habit at the base of the plant and an erect habit proximate the plant top.

Table 1 depicts expressions of morphological characteristics observed with respect to maize hybrid RPG824. The characteristics, expressions, and check cultivars listed follow the protocol specified by the French Ministry of Agriculture (Permanent Technical Committee for the Selection of Plant Varieties). Check cultivars indicated in Table 1 are exemplary of the expression for a given trait and also conform to the above-referenced protocol.

TABLE 1

MORPHOLOGICAL DESCRIPTION OF MAIZE HYBRID RPG824

| CHARACTERISTIC | EXPRESSION | CHECK CULTIVAR |
|---|---|---|
| Time of beginning of anthesis | early to medium (+1)* | F259 (4) |
| anthocyanin coloration of silks | present | F2 (9) |
| length of plant (tassel included) | medium (+15) | Magister (5) |
| type of grain (in middle third of ear) | dent-like | F259 (4) |
| anthocyanin coloration of glumes of the cob | absent | F2 (1) |

*Deviation from check cultivar.

Tables 2A and 2B depict isozyme profiles of the parent inbred lines to maize hybrid RPG824 (RPK7346, RPK7250), thereby profiling isozyme alleles thereof. Data within Tables 2A and 2B were generated using a protocol such as that described by Stuber et al., "Techniques and Scoring Procedures for Starch Gel Electrophoresis of Enzymes from Maize (*Zea mays* L.)," Technical Bulletin No. 286, North Carolina Agricultural Research Service, North Carolina State University, Raleigh, N.C. (1988), hereby incorporated by reference.

TABLE 2A

RPK7346 ISOZYME PROFILE

| ISOZYME | LOCUS | CHROMOSOME | ALLELE |
|---|---|---|---|
| MDH | 1 | 8 | 6 |
|  | 2 | 6 | 6 |
|  | 3 | 3 | 16 |
|  | Mmm | 1 | M |
|  | 4 | 1 | 12 |
|  | 5 | 5 | 12 |

TABLE 2A-continued

RPK7346 ISOZYME PROFILE

| ISOZYME | LOCUS | CHROMOSOME | ALLELE |
|---|---|---|---|
| IDH | 1 | 8 | 6 |
|  | 2 | 6 | 6 |
| PGI | 1 | 1 | 4 |
| PGD | 1 | 6 | 3,8 |
|  | 2 | 3 | 5 |
| PGM | 1 | 1 | 9 |
|  | 2 | 5 | 4 |
| ACP | 1 | 9 | 2 |
| DIA | 1 | 2 | 8 |
| ADH | 1 | 1 | 4 |
| GOT | 1 | 3 | 4 |
|  | 2 | 5 | 4 |
|  | 3 | 5 | 4 |
| βGLU | 1 | 10 | 6 |
| CAT | 3 | 4 | 12 |

TABLE 2B

RPK7250 ISOZYME PROFILE

| ISOZYME | LOCUS | CHROMOSOME | ALLELE |
|---|---|---|---|
| MDH | 1 | 8 | 6 |
|  | 2 | 6 | 6 |
|  | 3 | 3 | 18 |
|  | Mmm | 1 | M |
|  | 4 | 1 | 12 |
|  | 5 | 5 | 12 |
| IDH | 1 | 8 | 4 |
|  | 2 | 6 | 6 |
| PGI | 1 | 1 | 4 |
| PGD | 1 | 6 | 3,8 |
|  | 2 | 3 | 5 |
| PGM | 1 | 1 | 9 |
|  | 2 | 5 | 4 |
| ACP | 1 | 9 | 4 |
| DIA | 1 | 2 | 8 |
| ADH | 1 | 1 | 4 |
| GOT | 1 | 3 | 4 |
|  | 2 | 5 | 2 |
|  | 3 | 5 | 4 |
| βGLU | 1 | 10 | 6 |
| CAT | 3 | 4 | 9 |

Tables 3, 4A, and 4B depict the RFLP profile of maize hybrid RPG824. Table 3 depicts the RFLP profile of maize hybrid RPG824 via the RFLP profiles of maize inbreds RPK7346 and RPK7250. Tables 4A and 4B further augment Table 3 by listing inbreds having the same RFLP alleles and inbreds having different RFLP alleles as maize hybrid RPG824.

TABLE 3

RFLP PROFILE OF MAIZE HYBRID RPG824 AND COMPARISON TO 12 REFERENCE INBREDS

| Maize DB | Nb of allele | RPK7346 | RPK7250 | A619 | A632 | B73 | CM105 | CO255 | EP1 | F2 | F252 | LO904 | MO17 | OH43 | W401 |
|---|---|---|---|---|---|---|---|---|---|---|---|---|---|---|---|
| UMC94A | 5 | n | 2 | 1 | 5 | 2 | 2 | n | n | 2 | 2 | 2 | 4 | 1 | 5 |
| UMC11 | 8 | 51 | 51 | 41 | 51 | 14 | 51 | 51 | 93 | 51 | 72 | 51 | 82 | 35 | 23 |
| UMC157 | 7 | 434 | 324 | 342 | 123 | 324 | 123 | 434 | 434 | 143 | 343 | 324 | 123 | 342 | 251 |
| UMC76 | 7 | 52 | 45 | 33 | 56 | 33 | 45 | 42 | 52 | 42 | 33 | 51 | 24 | 33 | 24 |
| CSU59B | 3 | 1 | 1 | 1 | 1 | 2 | 1 | 1 | 1 | 2 | 2 | 1 | 3 | 1 | 1 |
| UMC58 | 4 | 31 | 22 | 22 | 32 | 32 | 32 | 33 | 33 | 31 | 32 | 32 | 31 | 22 | 33 |
| UMC67 | 8 | 31 | 33 | 34 | 33 | 33 | 33 | 28 | 28 | 11 | 38 | 33 | 32 | 34 | 37 |
| BNL5.59 | 7 | 411 | 412 | 212 | 411 | 514 | 411 | 514 | 514 | 512 | 312 | 514 | 413 | 212 | 413 |
| UMC83A | 6 | 41 | 12 | 52 | 12 | 62 | 12 | 31 | 31 | 22 | 62 | 62 | 12 | 52 | 22 |
| UMC128 | 7 | 355 | 122 | 152 | 122 | 122 | 154 | 132 | 132 | 133 | 252 | 122 | 152 | 1582 | 154 |
| UMC107A | 3 | 3 | 1 | 1 | 1 | 1 | 1 | 1 | 1 | 1 | 1 | 1 | 2 | 1 | 1 |

TABLE 3-continued

RFLP PROFILE OF MAIZE HYBRID RPG824 AND COMPARISON TO 12 REFERENCE INBREDS

| Maize DB | Nb of allele | RPK7346 | RPK7250 | A619 | A632 | B73 | CM105 | CO255 | EP1 | F2 | F252 | LO904 | MO17 | OH43 | W401 |
|---|---|---|---|---|---|---|---|---|---|---|---|---|---|---|---|
| UMC84 | 10 | 72 | 34 | 55 | 63 | 11 | 35 | 43 | 21 | 11 | 72 | 12 | 71 | 55 | 43 |
| UMC161 | 5 | 123 | 137 | 137 | 137 | 223 | 137 | 122 | 122 | 223 | 137 | 223 | 137 | 137 | 228 |
| BNL6.32 | 8 | 243 | 333 | 162 | 521 | 351 | 521 | 461 | 271 | 333 | 271 | 351 | 161 | 162 | 461 |
| BNL7.49B | 2 | 1 | 1 | 1 | 1 | 1 | 1 | 1 | 1 | 2 | 1 | 1 | 1 | 1 | 1 |
| UMC6 | 7 | 531 | nnn | 531 | 521 | 521 | 521 | 531 | 231 | 612 | 134 | 531 | 521 | 531 | 212 |
| CSU109 | 10 | 22 | 65 | 72 | 22 | 61 | 61 | 35 | 53 | 41 | 94 | 61 | 81 | 55 | 72 |
| UMC121 | 6 | 36 | 36 | 51 | n2 | 36 | 17 | 36 | 36 | 53 | 44 | 36 | 51 | 51 | 17 |
| UMC32A | 5 | 31 | 31 | 31 | 31 | 31 | 31 | 23 | 23 | 14 | 34 | 31 | 31 | 32 | 31 |
| CSU16A | 8 | 53 | 25 | 21 | 53 | 21 | 33 | 44 | 15 | 42 | 44 | 21 | 41 | 21 | 44 |
| UMC10A | 7 | 22 | 23 | 31 | 43 | 43 | 473 | 33 | 12 | 23 | 52 | 43 | 52 | 31 | 23 |
| UMC92 | 7 | 11 | 11 | 21 | 13 | 73 | 73 | 32 | 21 | 62 | 51 | 73 | 73 | 21 | 62 |
| UMC102 | 5 | n3 | n4 | n4 | n4 | n4 | n4 | 32 | 11 | n4 | n4 | n4 | 24 | n4 | n4 |
| CSU30A | 4 | 42 | 24 | 24 | 11 | 147 | 11 | 42 | 42 | 42 | 11 | 14 | 42 | 24 | 11 |
| UMC60 | 3 | 3 | 3 | 3 | 3 | 3 | 3 | 3 | 1 | 3 | 2 | 3 | 1 | 3 | 3 |
| BNL8.01 | 6 | 3 | 1 | 1 | 2 | 6 | 6 | 2 | 3 | 4 | 5 | 6 | 6 | 2 | 5 |
| UMC16A | 4 | 23 | 22 | 23 | 23 | 22 | 23 | n4 | n4 | 13 | 23 | 22 | 23 | 23 | 23 |
| CSU25A | 4 | 4 | 4 | 2 | 4 | 2 | 4 | 3 | 3 | 1 | 4 | 2 | 4 | 2 | 1 |
| UMC31 | 2 | 4 | 4 | 4 | 4 | 4 | 4 | 4 | 4 | 4 | 4 | 4 | 1 | 4 | 4 |
| CSU19 | 4 | 3 | 4 | 2 | 3 | 1 | 1 | 4 | 4 | 3 | 1 | 3 | 3 | 2 | 3 |
| BNL15.45 | 5 | 3 | 5 | 2 | 5 | 4 | 5 | n | n | n | 5 | 4 | 2 | 2 | 2 |
| UMC19 | 6 | 15 | 32 | 44 | 24 | 11 | 24 | 11 | 26 | 26 | 11 | 11 | 24 | 44 | 44 |
| UMC66 | 5 | 41 | 23 | 34 | 12 | 12 | 12 | 24 | 34 | 23 | 34 | 12 | 23 | 34 | 12 |
| UMC104B | 3 | 2 | 2 | 1 | 2 | 3 | 2 | 2 | 3 | 2 | 3 | 3 | 3 | 1 | 3 |
| CSU9B | 4 | 222 | 122 | 312 | 312 | 232 | 232 | 222 | 232 | 232 | 222 | 232 | 222 | 312 | 232 |
| UMC15 | 4 | 3 | 3 | 3 | 3 | 4 | 3 | 4 | 3 | 3 | 2 | 4 | 1 | 3 | 3 |
| BNL15.07 | 6 | 5 | 2 | 3 | 6 | 4 | 6 | 3 | 4 | 1 | 5 | 4 | 3 | 3 | 2 |
| BNL6.25 | 6 | 12 | 56 | 34 | 56 | 56 | 56 | 45 | 56 | 33 | 56 | 56 | 24 | 34 | 56 |
| UMC107B | 5 | 43 | 52 | 43 | 52 | 43 | 52 | 43 | 43 | 51 | 35 | 43 | 11 | 43 | 43 |
| UMC27 | 4 | 3 | 2 | 2 | 3 | 3 | 2 | 6 | 6 | 6 | 4 | 3 | 3 | 2 | 4 |
| UMC43 | 5 | 26 | 13 | 13 | 13 | 17 | 13 | 13 | 15 | 26 | 13 | 17 | 32 | 13 | 13 |
| UMC83B | 5 | 1 | 2 | 5 | 3 | 2 | 3 | 4 | 1 | 1 | 4 | 2 | 3 | 5 | 4 |
| CSU36A | 3 | 2 | 2 | 2 | 2 | 3 | 2 | 1 | 2 | 2 | 2 | 3 | 3 | 2 | 3 |
| UMC138B | 3 | 1 | 3 | 1 | 2 | 3 | 3 | 3 | 3 | 1 | 1 | 3 | 2 | 3 | 3 |
| UMC54 | 7 | 25 | 25 | 53 | 21 | 43 | 41 | 14 | 33 | 14 | 43 | 43 | 25 | 25 | 25 |
| UMC68 | 6 | 32 | 22 | 45 | 42 | 43 | 42 | 46 | 46 | 45 | 46 | 22 | 43 | 46 | 32 |
| UMC104A | 4 | 32 | 11 | 21 | 21 | 21 | 21 | 33 | 32 | 11 | 21 | 21 | 32 | 21 | 32 |
| UMC59 | 6 | 62 | 15 | 21 | 21 | 31 | 21 | 44 | 15 | 62 | 15 | 31 | 31 | 15 | 43 |
| UMC65 | 3 | 43 | 22 | 22 | 22 | 22 | 22 | 43 | 22 | 42 | 42 | 22 | 43 | 22 | 43 |
| UMC21 | 7 | 5n2 | 5n2 | 115 | 2n3 | 2n3 | 2n3 | 5n2 | 5n4 | 331 | 321 | 2n3 | 636 | 115 | 2n3 |
| CSU60 | 4 | 2 | 6 | 3 | 6 | 6 | 6 | 3 | 6 | 1 | 1 | 6 | 6 | 3 | 1 |
| UMC38A | 5 | 34 | 23 | 25 | 23 | 24 | 23 | 23 | 23 | 41 | 23 | 24 | 24 | 23 | 23 |
| UMC138A | 7 | 24 | 25 | 25 | 25 | 25 | 25 | 41 | 16 | 23 | 23 | 25 | 21 | 33 | 33 |
| UMC132A | 5 | 24 | 25 | 24 | 25 | 25 | 25 | 23 | 24 | 13 | 23 | 25 | 12 | 23 | 23 |
| CSU16B | 5 | 3 | 4 | 1 | 4 | 4 | 4 | 3 | 4 | 3 | 2 | 4 | 5 | 1 | 1 |
| UMC62 | 5 | 222 | 222 | 121 | 222 | 114 | 222 | 224 | 222 | 224 | 122 | 114 | 222 | 224 | 121 |
| UMC134A | 6 | 35 | 35 | 35 | 35 | 23 | 35 | 23 | 12 | 11 | 14 | 35 | 35 | 34 | 23 |
| BNL8.45 | 5 | 36 | 23 | 23 | 23 | 25 | 15 | 23 | 25 | 34 | 36 | 25 | 25 | 23 | 23 |
| BNL15.40 | 5 | 34 | 21 | 21 | 21 | 23 | 13 | 21 | 23 | 42 | 34 | 23 | 23 | 21 | 21 |
| CSU11 | 7 | 2 | 4 | 1 | 4 | 4 | 3 | 1 | 1 | 5 | 8 | 4 | 6 | 1 | 1 |
| BNL15.21 | 3 | 2 | 2 | 4 | 2 | 2 | 2 | 4 | 4 | 3 | 2 | 2 | 4 | 2 | 2 |
| UMC110 | 8 | n62 | 513 | 245 | 513 | 514 | 513 | n14 | 371 | n14 | 285 | n62 | 245 | 245 | 24n |
| UMC116 | 7 | 32 | 4n | 4n | 4n | 61 | 4n | 4n | 63 | 44 | 51 | 4n | 24 | 4n | 4n |
| BNL14.07 | 7 | 18 | 55 | 32 | 28 | 17 | 55 | 18 | 18 | 18 | 43 | 55 | 17 | 56 | 17 |
| BNL16.06 | 4 | 1 | 3 | 1 | 3 | 3 | 3 | 1 | 2 | 2 | c | 3 | 3 | 1 | 1 |
| UMC168 | 8 | 412 | 422 | 414 | 131 | 131 | 131 | 613 | 613 | 513 | 113 | 131 | 423 | 414 | 423 |
| CSU27 | 6 | 1n5 | 2n1 | 4n4 | 327 | 327 | 327 | 2n1 | 326 | 126 | 4n4 | 327 | 327 | 4n4 | 4n4 |
| UMC35 | 5 | n2 | 32 | 22 | n2 | 32 | n2 | n2 | n2 | n1 | n2 | 32 | 11 | 22 | n2 |
| CSU163 | 9 | 81 | 42 | 81 | 54 | 81 | 54 | 15 | 63 | 22 | 41 | 81 | 51 | 81 | 61 |
| UMC103 | 6 | 27 | 36 | 27 | 27 | 27 | 28 | 34 | 34 | 36 | 35 | 27 | 27 | 27 | 31 |
| UMC120 | 3 | 21 | 11 | 11 | 21 | 2n | 21 | 21 | 21 | 21 | 11 | 2n | 11 | 11 | 11 |
| UMC124 | 3 | 3 | 3 | 3 | 1 | 3 | 3 | 3 | 3 | 3 | 3 | 1 | 3 | 3 | 2 |
| UMC152 | 6 | 13 | 61 | 61 | 14 | 61 | 14 | 31 | 31 | 61 | 25 | 61 | 61 | 61 | 11 |
| UMC32B | 3 | 22 | 22 | 22 | 22 | 21 | 22 | 22 | 22 | 33 | 33 | 21 | 22 | 22 | 22 |
| UMC89 | 4 | 22 | 24 | 23 | 23 | 23 | 23 | 23 | 22 | 23 | 15 | 23 | 24 | 23 | 23 |
| UMC12A | 5 | 4 | 3 | 4 | 5 | 1 | 4 | 4 | 2 | 4 | 3 | 1 | 3 | 1 | 4 |
| UMC16B | 10 | 515 | 422 | 312 | 142 | 514 | 146 | 113 | 143 | 611 | 146 | 514 | 515 | 146 | 136 |
| UMC7 | 5 | 2 | 5 | 2 | 1 | 1 | 1 | 6 | 7 | 1 | 7 | 1 | 2 | 2 | 2 |
| UMC109 | 5 | 4 | 3 | 1 | 3 | 4 | 3 | 2 | 1 | 5 | 2 | 4 | 2 | 1 | 5 |
| UMC113A | 7 | 61 | 42 | 42 | 42 | 42 | 42 | 31 | 22 | 12 | 32 | 42 | 42 | 42 | 62 |
| UMC81 | 4 | 22 | 23 | 32 | 12 | 32 | 12 | 23 | 22 | 32 | 32 | 32 | 23 | 32 | 22 |
| UMC114 | 8 | 623 | 346 | 624 | 575 | 476 | 575 | 637 | 575 | 152 | 162 | 476 | 623 | 624 | 623 |
| UMC95 | 8 | 65 | 11 | 23 | 45 | 11 | 22 | 5n | 11 | 34 | 44 | 11 | 45 | 23 | 5n |
| BNL6.09 | 4 | 2 | 3 | 3 | 3 | 4 | 3 | 2 | 2 | 3 | 1 | 4 | 3 | 3 | 1 |
| BNL14.28A | 5 | 43 | 51 | 42 | 42 | 42 | 42 | 11 | 11 | 42 | 42 | 42 | 52 | 42 | 51 |

TABLE 3-continued

RFLP PROFILE OF MAIZE HYBRID RPG824 AND COMPARISON TO 12 REFERENCE INBREDS

| Maize DB | Nb of allele | RPK7346 | RPK7250 | A619 | A632 | B73 | CM105 | CO255 | EP1 | F2 | F252 | LO904 | MO17 | OH43 | W401 |
|---|---|---|---|---|---|---|---|---|---|---|---|---|---|---|---|
| CSU59A | 8 | 343 | 1n1 | 1n1 | 141 | 424 | 141 | 211 | 111 | 145 | 531 | 424 | 141 | 1n1 | 111 |
| CSU25B | 3 | 2 | 2 | 2 | 2 | 2 | 2 | 2 | 2 | 2 | 3 | 2 | 2 | 1 | 2 | 3 |
| BNL3.04 | 9 | 21 | 13 | 13 | 22 | 22 | 22 | 33 | 12 | 22 | 44 | 22 | 24 | 25 | 26 |
| UMC130 | 8 | 21 | 72 | 32 | 32 | 83 | 73 | 72 | 21 | 34 | 73 | 83 | 1n | 32 | 54 |
| BNL10.13 | 5 | 6 | 3 | 1 | 6 | 1 | 6 | 2 | 4 | 6 | 4 | 1 | 6 | 1 | 6 |
| UMC44A | 7 | 132 | 811 | 825 | 544 | 544 | 544 | 132 | 355 | 132 | A65 | 544 | 213 | 825 | 825 |
| BNL7.49A | 2 | 4 | 3 | 3 | 3 | 3 | 3 | 4 | 4 | 3 | 4 | 3 | 4 | 3 | 4 |
| CSU48 | 8 | 13 | 47 | 52 | 16 | 16 | 26 | 21 | 52 | 44 | 16 | 16 | 44 | 52 | 35 |

TABLE 4A

MAIZE HYBRID RPG824 RFLP PROFILE

| Maize DB | Inbreds having same allele | | | | | | | | | |
|---|---|---|---|---|---|---|---|---|---|---|
| UMC94A | B73 | CM105 | CO255 | EP1 | F2 | F252 | ILO904 | | | |
| UMC11 | A632 | CM105 | CO255 | F2 | ILO904 | | | | | |
| UMC157 | B73 | CO255 | EP1 | ILO904 | | | | | | |
| UMC76 | CM105 | EP1 | | | | | | | | |
| CSUS9B | A619 | A632 | CM106 | CO255 | EP1 | ILO904 | OH43 | W401 | | |
| UMC58 | A619 | F2 | MO17 | OH43 | | | | | | |
| UMC67 | A632 | B73 | CM105 | ILO904 | | | | | | |
| BNL5.59 | A632 | CM105 | | | | | | | | |
| UMC83A | A632 | CM105 | MO17 | | | | | | | |
| UMC128 | A632 | B73 | ILO904 | | | | | | | |
| UMC107A | A619 | A632 | B73 | CM105 | CO255 | EP1 | F2 | F252 | ILO904 | OH43 | W401 |
| UMC84 | F252 | | | | | | | | | |
| UMC161 | A619 | A632 | CM105 | F252 | MO17 | OH43 | | | | |
| BNL6.32 | F2 | | | | | | | | | |
| BNL7.49B | A619 | A632 | B73 | CM105 | CO255 | EP1 | F252 | ILO904 | MO17 | OH43 | W401 |
| UMC6 | A619 | CO255 | ILO904 | OH43 | | | | | | |
| UMC44B | F252 | MO17 | | | | | | | | |
| UMC34 | AS619 | MO17 | OH43 | W401 | | | | | | |
| UMC131 | A632 | | | | | | | | | |
| UMC139 | A632 | B73 | CM105 | F252 | ILO904 | MO17 | | | | |
| UMC4 | CM105 | CO255 | | | | | | | | |
| UMC137 | A632 | CM105 | MO17 | W401 | | | | | | |
| UMC36A | A619 | F252 | W401 | | | | | | | |
| CSU109 | A632 | | | | | | | | | |
| UMC121 | B73 | CO255 | EP1 | ILO904 | | | | | | |
| UMC32A | A619 | A632 | B73 | CM105 | ILO904 | MO17 | W401 | | | |
| CSU16A | A632 | | | | | | | | | |
| UMC10A | F2 | W401 | | | | | | | | |
| UMC92 | | | | | | | | | | |
| UMC102 | A619 | A632 | B73 | CM105 | F2 | F252 | ILO904 | OH43 | W401 | |
| CSU30A | A619 | CO255 | EP1 | F2 | MO17 | OH43 | | | | |
| UMC60 | A619 | A632 | B73 | CM105 | CO255 | F2 | ILO904 | OH43 | W401 | |
| BNL8.01 | A619 | EP1 | | | | | | | | |
| UMC16A | A619 | A632 | B73 | CM105 | F252 | ILO904 | MO17 | OH43 | W401 | |
| CSU25A | A632 | CM105 | F252 | MO17 | | | | | | |
| UMC31 | A619 | A632 | B73 | CM105 | CO255 | EP1 | F2 | F252 | ILO904 | OH43 | W401 |
| CSU19 | A632 | CO255 | EP1 | F2 | ILO904 | MO17 | W401 | | | |
| BNL15.45 | A632 | CM105 | F252 | | | | | | | |
| UMC19 | | | | | | | | | | |
| UMC66 | F2 | MO17 | | | | | | | | |
| UMC104B | A632 | CM105 | CO255 | F2 | | | | | | |
| CSU9B | CO255 | F252 | MO17 | | | | | | | |
| UMC15 | A619 | A632 | CM105 | EP1 | F2 | OH43 | W401 | | | |
| BNL15.07 | F252 | W401 | | | | | | | | |
| BNL6.25 | A632 | B73 | CM105 | EP1 | F252 | ILO904 | W401 | | | |
| UMC107B | A619 | A632 | B73 | CM105 | CO255 | EP1 | ILO904 | OH43 | W401 | |
| UMC27 | A619 | A632 | B73 | CM105 | ILO904 | MO17 | OH43 | | | |
| UMC43 | A619 | A632 | CM105 | CO255 | F2 | F252 | OH43 | W401 | | |
| UMC83B | B73 | EP1 | F2 | ILO904 | | | | | | |
| CSU36A | A619 | A632 | CM105 | EP1 | F2 | F252 | OH43 | | | |
| UMC138B | A619 | B73 | CM105 | CO255 | EP1 | F2 | F252 | ILO904 | OH43 | W401 |
| UMC54 | MO17 | OH43 | W401 | | | | | | | |
| UMC68 | ILO904 | W401 | | | | | | | | |
| UMC104A | EP1 | F2 | MO17 | W401 | | | | | | |
| UMCS9 | EP1 | F2 | F252 | OH43 | | | | | | |
| UMC65 | A619 | A632 | B73 | CM105 | CO255 | EP1 | ILO904 | MO17 | OH43 | W401 |

TABLE 4A-continued

MAIZE HYBRID RPG824 RFLP PROFILE

| Maize DB | Inbreds having same allele | | | | | | | | | |
|---|---|---|---|---|---|---|---|---|---|---|
| UMC21 | CO255 | | | | | | | | | |
| CSU60 | A632 | B73 | CM105 | EP1 | ILO904 | MO17 | | | | |
| UMC38A | A632 | CM105 | CO255 | EP1 | F252 | OH43 | W401 | | | |
| UMC138A | A619 | A632 | B73 | CM105 | ILO904 | | | | | |
| UMC132A | A619 | A632 | B73 | CM105 | EP1 | ILO904 | | | | |
| CSU16B | A632 | B73 | CM105 | CO255 | EP1 | F2 | ILO904 | | | |
| UMC62 | A632 | CM105 | EP1 | MO17 | | | | | | |
| UMC134A | A619 | A632 | CM105 | ILO904 | MO17 | | | | | |
| BNL8.45 | A619 | A632 | CO255 | F252 | OH43 | W401 | | | | |
| BNL15.40 | A619 | A632 | CO255 | F252 | OH43 | W401 | | | | |
| CSU11 | A632 | B73 | ILO904 | | | | | | | |
| BNL15.21 | A632 | B73 | CM105 | F252 | ILO904 | OH43 | W401 | | | |
| UMC110 | A632 | CM105 | ILO904 | | | | | | | |
| UMC116 | A619 | A632 | CM105 | CO255 | ILO904 | OH43 | W401 | | | |
| BNL14.07 | CM105 | CO255 | EP1 | F2 | ILO904 | | | | | |
| BNL16.06 | A619 | A632 | B73 | CM105 | CO255 | ILO904 | MO17 | OH43 | W401 | |
| UMC168 | | | | | | | | | | |
| CSU27 | CO255 | | | | | | | | | |
| UMC35 | A632 | B73 | CM105 | CO255 | EP1 | F252 | ILO904 | W401 | | |
| CSU163 | A629 | B73 | ILO904 | OH43 | | | | | | |
| UMC103 | A619 | A632 | B73 | F2 | ILO904 | MO17 | OH43 | | | |
| UMC120 | A619 | A632 | CM105 | CO255 | EP1 | F2 | F252 | MO17 | OH43 | W401 |
| UMC124 | A632 | B73 | CM105 | CO255 | EP1 | F2 | ILO904 | MO17 | | |
| UMC152 | A619 | B73 | F2 | ILO904 | MO17 | OH43 | | | | |
| UMC32B | A619 | A632 | CM105 | CO255 | EP1 | MO17 | OH43 | W401 | | |
| UMC89 | EP1 | MO17 | | | | | | | | |
| UMC12A | A619 | CM105 | CO255 | F2 | F252 | MO17 | W401 | | | |
| UMC16B | MO17 | | | | | | | | | |
| UMC7 | A619 | MO17 | OH43 | W401 | | | | | | |
| UMC109 | A632 | B73 | CM105 | ILO904 | | | | | | |
| UMC113A | A619 | A632 | B73 | CM105 | ILO904 | MO17 | OH43 | | | |
| UMC81 | CO255 | EP1 | MO17 | W401 | | | | | | |
| UMC114 | MO17 | W401 | | | | | | | | |
| UMC95 | B73 | EP1 | ILO904 | | | | | | | |
| BNL6.09 | A619 | A632 | CM105 | CO255 | EP1 | F2 | MO17 | OH43 | | |
| BNL14.28A | W401 | | | | | | | | | |
| CSU59A | A619 | OH43 | | | | | | | | |
| CSU25B | A619 | A632 | B73 | CM105 | CO255 | EP1 | F252 | ILO904 | OH43 | |
| BNL3.04 | A619 | | | | | | | | | |
| UMC130 | CO255 | EP1 | | | | | | | | |
| BNL10.13 | A632 | CM105 | F2 | MO17 | W401 | | | | | |
| UMC44A | CO255 | F2 | | | | | | | | |
| BNL7.49A | A619 | A632 | B73 | CM105 | CO255 | EP1 | F2 | F252 | ILO904 | MO17 | OH43 | W401 |
| CSU48 | | | | | | | | | | |

TABLE 4B

RPG824 RFLP PROFILE

| MaizeDB | Inbreds having different alleles | | | | | | | | | |
|---|---|---|---|---|---|---|---|---|---|---|
| UMC94A | A619 | A632 | MO17 | OH43 | W401 | | | | | |
| UMC11 | A619 | B73 | EP1 | F252 | MO17 | OH43 | W401 | | | |
| UMC157 | A619 | A632 | CM105 | F2 | F252 | MO17 | OH43 | W401 | | |
| UMC76 | A619 | A632 | B73 | CO255 | F2 | F252 | ILO904 | MO17 | OH43 | W401 |
| CSU59B | B73 | F2 | F252 | MO17 | | | | | | |
| UMC58 | A632 | B73 | CM105 | CO255 | EP1 | F252 | ILO904 | | | |
| UMC67 | A619 | CO255 | EP1 | F2 | F252 | MO17 | OH43 | W401 | | |
| BNL5.59 | A619 | B73 | CO255 | EP1 | F2 | F252 | ILO904 | MO17 | OH43 | W401 |
| UMC83A | A619 | B73 | CO255 | EP1 | F2 | F252 | ILO904 | OH43 | W401 | |
| UMC128 | A619 | CM105 | CO255 | EP1 | F2 | F252 | MO17 | OH43 | W401 | |
| UMC107A | MO17 | | | | | | | | | |
| UMC84 | A619 | A632 | B73 | CM105 | CO255 | EP1 | F2 | ILO904 | MO17 | OH43 | W401 |
| UMC161 | B73 | CO255 | EP1 | F1 | ILO904 | W401 | | | | |
| BNL6.32 | A619 | A632 | B73 | CM105 | CO255 | EP1 | F252 | ILO904 | MO17 | OH43 | W401 |
| BNL7.49B | F2 | | | | | | | | | |
| UMC6 | A632 | B73 | CM105 | EP1 | F2 | F252 | MO17 | W401 | | |
| UMC44B | A619 | A632 | B73 | CM105 | CO255 | EP1 | F2 | ILO904 | OH43 | W401 |
| UMC34 | A632 | B73 | CM105 | CO255 | EP1 | F2 | F252 | ILO904 | | |
| UMC131 | A619 | B73 | CM105 | CO255 | EP1 | F2 | F252 | ILO904 | MO17 | OH43 | W401 |
| UMC139 | A619 | CO255 | EP1 | F2 | OH43 | W401 | | | | |
| UMC4 | A619 | A632 | B73 | EP1 | F252 | ILO904 | MO17 | OH43 | W401 | |

TABLE 4B-continued

RPG824 RFLP PROFILE

| MaizeDB | \multicolumn{12}{c}{Inbreds having different alleles} | | | | | | | | | | | |
|---|---|---|---|---|---|---|---|---|---|---|---|---|
| UMC137 | A619 |  | B73 |  | CO255 | EP1 | F2 | F252 | ILO904 |  | OH43 |  |
| UMC36A |  | A632 | B73 | CM105 | CO255 | EP1 | F2 |  | ILO904 | MO17 | OH43 |  |
| CSU109 | A619 |  | B73 | CM105 | CO255 | EP1 | F2 | F252 | ILO904 | MO17 | OH43 | W401 |
| UMC121 | A619 | A632 |  | CM105 |  |  | F2 | F252 |  | MO17 | OH43 | W401 |
| UMC32A |  |  |  |  | CO255 | EP1 | F2 | F252 |  |  | OH43 |  |
| CSU16A | A619 |  | B73 | CM105 | CO255 | EP1 | F2 | F252 | ILO904 | MO17 | OH43 | W401 |
| UMC10A | A619 | A632 | B73 | CM105 | CO255 | EP1 | F2 |  | ILO904 | MO17 | OH43 |  |
| UMC92 | A619 | A632 | B73 | CM105 | CO255 | EP1 | F2 | F252 | ILO904 | MO17 | OH43 | W401 |
| UMC102 |  |  |  |  | CO255 | EP1 |  |  |  | MO17 |  |  |
| CSU30A |  | A632 | B73 | CM105 |  |  |  | F252 | ILO904 |  |  | W401 |
| UMC60 |  |  |  |  |  | EP1 |  | F252 |  | MO17 |  |  |
| BNL8.01 |  | A632 | B73 | CM105 | CO255 |  | F2 | F252 | ILO904 | MO17 | OH43 | W401 |
| UMC16A |  |  |  |  | CO255 | EP1 | F2 |  |  |  |  |  |
| CSU25A | A619 |  | B73 |  | CO255 | EP1 | F2 |  | ILO904 |  | OH43 | W401 |
| UMC31 |  |  |  |  |  |  |  |  |  | MO17 |  |  |
| CSU19 | A619 |  | B73 | CM105 |  |  |  | F252 |  |  | OH43 |  |
| BNL15.45 | A619 |  | B73 |  | CO255 | EP1 | F2 |  | ILO904 | MO17 | OH43 | W401 |
| UMC19 | A619 | A632 | B73 | CM105 | CO255 | EP1 | F2 | F252 | ILO904 | MO17 | OH43 | W401 |
| UMC66 | A619 | A632 | B73 | CM105 | CO255 | EP1 |  | F252 | ILO904 |  | OH43 | W401 |
| UMC104B | A619 |  | B73 |  |  | EP1 |  | F252 | ILO904 | MO17 | OH43 | W401 |
| CSU9B | A619 | A632 | B73 | CM105 |  | EP1 | F2 |  | ILO904 |  | OH32 | W401 |
| UMC15 |  |  | B73 |  | CO255 |  |  | F252 | ILO904 | MO17 |  |  |
| BNL15.07 | A619 | A632 | B73 | CM105 | CO255 | EP1 | F2 |  | ILO904 | MO17 | OH43 |  |
| BNL6.25 | A619 |  |  |  | CO255 |  | F2 |  |  | MO17 | OH43 |  |
| UMC107B |  |  |  |  |  |  | F2 | F252 |  | MO17 |  |  |
| UMC27 |  |  |  |  | CO255 | EP1 | F2 | F252 |  |  |  | W401 |
| UMC43 |  |  | B73 |  |  | EP1 |  |  | ILO904 | MO17 |  |  |
| UMC83B | A619 | A632 |  | CM105 | CO255 |  |  | F252 |  | MO17 | OH43 | W401 |
| CSU36A |  |  | B73 |  | CO255 |  |  |  | ILO904 | MO17 |  | W401 |
| UMC138B |  | A632 |  |  |  |  |  |  |  | MO17 |  |  |
| UMC54 | A619 | A632 | B73 | CM105 | CO255 | EP1 | F2 | F252 | ILO904 |  |  |  |
| UMC68 | A619 | A632 | B73 | CM105 |  | EP1 | F2 | F252 |  | MO17 | OH43 |  |
| UMC104A | A619 | A632 | B73 | CM105 | CO255 |  |  | F252 | ILO904 |  | OH43 |  |
| UMC59 | A619 | A632 | B73 | CM105 | CO255 |  |  |  | ILO904 | MO17 |  | W401 |
| UMC65 |  |  |  |  |  |  | F2 | F252 |  |  |  |  |
| UMC21 | A619 | A632 | B73 | CM105 |  | EP1 | F2 | F252 | ILO904 | MO17 | OH43 | W401 |
| CSU60 | A619 |  |  |  | CO255 |  | F2 | F252 |  |  | OH43 | W401 |
| UMC38A | A619 |  | B73 |  |  |  | F2 |  | ILO904 | MO17 |  |  |
| UMC138A |  |  |  |  | CO255 | EP1 | F2 | F252 |  | MO17 | OH43 | W401 |
| UMC132A |  |  |  |  | CO255 |  | F2 | F252 |  | MO17 | OH43 | W401 |
| CSU16B | A619 |  |  |  |  |  |  | F252 |  | MO17 | OH43 | W401 |
| UMC62 | A619 |  | B73 |  | CO255 |  | F2 | F252 | ILO904 |  | OH43 | W401 |
| UMC134A |  |  | B73 |  | CO255 | EP1 | F2 | F252 |  |  | OH43 | W401 |
| BNL8.45 |  |  | B73 | CM105 |  | EP1 | F2 |  | ILO904 | MO17 |  |  |
| BNL15.40 |  |  | B73 | CM105 |  | EP1 | F2 |  | ILO904 | MO17 |  |  |
| CSU11 | A619 |  |  | CM105 | CO255 | EP1 | F2 | F252 |  | MO17 | OH43 | W401 |
| BNL15.21 | A619 |  |  |  | CO255 | EP1 | F2 |  |  | MO17 |  |  |
| UMC110 | A619 |  | B73 |  | CO255 | EP1 | F2 | F252 |  | MO17 | OH43 | W401 |
| UMC116 |  |  | B73 |  |  | EP1 | F2 | F252 |  | MO17 |  |  |
| BNL14.07 | A619 | A632 | B73 |  |  |  |  | F252 |  | MO17 | OH43 | W401 |
| BNL16.06 |  |  |  |  |  | EP1 | F2 | F252 |  |  |  |  |
| UMC168 | A619 | A632 | B73 | CM105 | CO255 | EP1 | F2 | F252 | ILO904 | MO17 | OH43 | W401 |
| CSU27 | 1619 | A632 | B73 | CM105 |  | EP1 | F2 | F252 | ILO904 | MO17 | OH43 | W401 |
| UMC35 | A619 |  |  |  |  |  | F2 |  |  | MO17 | OH43 |  |
| CSU163 |  | A632 |  | CM105 | CO255 | EP1 | F2 | F252 |  | MO17 |  | W401 |
| UMC103 |  |  |  | CM105 | CO255 | EP1 |  | F252 |  |  |  | W401 |
| UMC120 |  |  | B73 |  |  |  |  |  | ILO904 |  |  |  |
| UMC124 | A619 |  |  |  |  |  |  | F252 |  |  | OH43 | W401 |
| UMC152 |  | A632 |  | CM105 | CO255 | EP1 |  | F252 |  |  |  | W401 |
| UMC32B |  |  | B73 |  |  |  | F2 | F252 | ILO904 |  |  |  |
| UMC89 | A619 | A632 | B73 | CM105 | CO255 |  | F2 |  | ILO904 |  | OH43 | W401 |
| UMC12A |  | A632 | B73 |  |  | EP1 |  |  | ILO904 |  | OH43 |  |
| UMC16B | A619 | A632 | B73 | CM105 | CO255 | EP1 | F2 | F252 | ILO904 |  | OH43 | W401 |
| UMC7 |  | A632 | B73 | CM105 | CO255 | EP1 | F2 | F252 | ILO904 |  |  |  |
| UMC109 | A619 |  |  |  | CO255 | EP1 | F2 | F252 |  | MO17 | OH43 | W401 |
| UMC113A |  |  |  |  | CO255 | EP1 | F2 | F252 |  |  |  | W401 |
| UMC81 | A619 | A632 | B73 | CM105 |  |  | F2 | F252 | ILO904 |  | OH43 |  |
| UMC114 | A619 | A632 | B73 | CM106 | CO255 | EP1 | F2 | F252 | ILO904 |  | OH43 |  |
| UMC95 | A619 | A632 |  | CM105 | CO255 |  | F2 | F252 |  | MO17 | OH43 | W401 |
| BNL6.09 |  |  | B73 |  |  |  |  | F252 | ILO904 |  |  | W401 |
| BNL14.28A | A619 | A632 | B73 | CM105 | CO255 | EP1 | F2 | F252 | ILO904 | MO17 | OH43 |  |
| CSU59A |  | A632 | B73 | CM105 | CO255 | EP1 | F2 | F252 | ILO904 | MO17 |  | W401 |
| CSU25B |  |  |  |  |  |  | F2 |  |  | MO17 |  | W401 |
| BNL3.04 |  | A632 | B73 | CM105 | CO255 | EP1 | F2 | F252 | ILO904 | MO17 | OH43 | W401 |
| UMC130 | A619 | A632 | B73 | CM105 |  |  | F2 | F252 | ILO904 | MO17 | OH43 | W401 |

TABLE 4B-continued

RPG824 RFLP PROFILE

| MaizeDB | Inbreds having different alleles | | | | | | | | | | |
|---|---|---|---|---|---|---|---|---|---|---|---|
| BNL10.13 | A619 | B73 | CO255 | EP1 | F252 | ILO904 | OH43 | | | | |
| UMC44A | A619 | A632 | B73 | CM105 | EP1 | F252 | ILO904 | MO17 | OH43 | W401 | |
| BNL7.49A | | | | | | | | | | | |
| CSU48 | A619 | A632 | B73 | CM105 | CO255 | EP1 | F2 | F252 | ILO904 | MO17 | OH43 | W401 |

Table 5 depicts the seed sizing profile of maize hybrid RPG824. The seed sizing profile discloses the seed size and shape fractions as discard (plateless), rounds, and flats. Table 5 further discloses thousand kernel weights of the flat and round seed size fractions.

TABLE 5

MAIZE HYBRID RPG824 SEED SIZING PROFILE

| | |
|---|---|
| Round hole screen ($^{15.5}/_{64}$ inch): | = 18% discard |
| Slot screen ($^{14}/_{64}$ inch): | = 24% rounds |
| | = 58% flats |
| Thousand kernel weight: | |
| Flats | = 220 grams |
| Rounds | = 265 grams |

EXAMPLE 1

U.S. Hybrid Performance of RPG824

Table 6 depicts mean performance traits of maize hybrid RPG824 and two elite maize check hybrids over 15 locations in 1999 in the north central United States. P3893 and P3941 are the maize hybrids Pioneer 3893 and Pioneer 3941. Maize hybrid RPG824 had essentially the same harvest moisture, grain yield, stalk and root lodging percentages, and yield/moisture ratio as Pioneer 3893. However, RPG824 had a higher test weight, a higher plant height, and an ear height lower than that of either check hybrid.

EXAMPLE 2

Performance of Hybrid RPG824 at 14 Locations in North Central United States and Ontario

TABLE 6

HYBRID PERFORMANCE OF MAIZE HYBRID RPG824*
Year: 99 - State: US
Multilocation Analysis of 15 locations

| | MST (%) | sMST | YLD (bu/A) | sYLD | SL (%) | RL (%) | DE (%) | POP (x1000) | TW (lb/bu) | Y/M | PHT (in) | EHT (in) | FLM (days) | FLF (days) | HA (1–9) | EG (1–9) | SG (1–9) |
|---|---|---|---|---|---|---|---|---|---|---|---|---|---|---|---|---|---|
| RPG824 | 20.2 | 1.1 | 164 | 13 | 4 | 1 | 0 | 29 | 58 | 8.2 | 82 | 32 | 71 | 71 | 7 | 9 | 8 |
| P3893 | 20.1 | 0.7 | 162 | 11 | 3 | 1 | 0 | 28 | 56 | 8.2 | 78 | 39 | 72 | 72 | 8 | 9 | 8 |
| P3941 | 18.8 | 1.9 | 135 | 17 | 5 | 2 | 0 | 28 | 56 | 7.3 | 78 | 33 | 67 | 68 | 6 | 8 | 6 |
| --MEAN-- | 21.0 | | 152 | | 3 | 1 | 0 | 28 | 55 | 7.5 | 81 | 35 | 69 | 70 | 7 | 8 | 7 |
| --STD-DEV-- | 0.9 | | 13 | | 4 | 2 | 0 | 8 | 6 | 0.8 | | | 1 | 1 | | | |
| --CV-- | 4.5 | | 8 | | 140 | 239 | 690 | 29 | 10 | 10.4 | | | 1 | 1 | | | |

*P3893, Pioneer 3893;
P3941, Pioneer 3941;
RPG824, RPK7250*RPK7346;
MST, grain harvest moisture;
sMST, entry grain harvest moisture standard error;
YLD, grain yield adjusted to 15.5% grain moisture basis;
sYLD, entry grain yield standard error;
SL, stalks broken below the ear;
RL, stalks tilted greater than or equal to 15° from the vertical;
DE, stalks with dropped ears;
POP, plants/acre;
TW, grain test weight;
YM, ratio of YLD/MST;
PHT, plant height;
EHT, ear height;
FLM, number of days from planting in which 50% of plants shed pollen;
FLF, number of days from planting in which 50% of plants extruded silks;
HA, visual (1–9) rating for appearance at harvest, 1 = least preferred expression, 9 = most preferred expression for trait;
EG, visual (1–9) rating for early growth, 1 = least preferred expression, 9 = most preferred expression, for trait; and
SG, visual (1–9) rating for stay green trait observed in the fall before senescence, 1 = least preferred expression, 9 = most preferred expression, for trait.

Table 7 depicts the performance of maize hybrid RPG824 and check hybrids P3893 and G8975 at 14 locations in Minnesota, Wisconsin, South Dakota, and Ontario in 1999. G8975 is the maize hybrid Garst 8975. The grain yield, harvest moisture, stalk lodging score, root lodging score, and test weight of RPG824 were equal to, or better than, those of the check hybrids. The ear height of RPG824 was lower than that of Pioneer 3893 and slightly higher than that of Garst 8975. The plant height of RPG824 was higher than that of Pioneer 3893 but lower than that of Garst 8975.

TABLE 7*

Locations: (2 replications/location) 14 - MN, WI, SD, ONT - 1999

| HYBRID | YLD (bu/A) | MST (%) | SL (%) | RL (%) | TW (lb/bu) | EH/PH (in) |
|---|---|---|---|---|---|---|
| RPG824 | 163 | 19.8 | 3 | 2 | 58 | 28/74 |
| P3893 | 161 | 19.8 | 3 | 1 | 57 | 35/70 |
| G8975 | 148 | 18.9 | 3 | 1 | 56 | 26/84 |
| Mean | 151 | 20.6 | 3 | 1 | 56 | 32/76 |
| LSD (.05) | 2.8 | 0.7 | 3 | 1.5 | 6.5 | -/- |
| CV | 9 | 4.5 | 149 | 231 | 11 | -/- |

*RPG824, RPK7250*RPK7346;
P3893, Pioneer 3893;
G8975, Garst 8975;
YLD, grain yield adjusted to 15.5% grain moisture basis;
MST, grain moisture at harvest;
SL, percent plants broken below the ear at harvest;
RL, percent plants tilted at 15°, or more, from the vertical at harvest;
EH/PH, ear and plant height, respectively.

EXAMPLE 3
Performance of Maize Hybrid RPG824 in French Private Grain Trials

Tables 8–11 depict the performance of maize hybrid RPG824 in private French grain trials in 1997 and 1998. Table 8 depicts means of maize hybrid RPG824 and seven elite, check hybrids averaged over thirteen French locations in 1997. Grain moisture at harvest for RPG824 was significantly lower than those of Marignan, Twin, and Dea. The grain yield of maize hybrid RPG824 was significantly higher than that of any check hybrid. Maize hybrid RPG824 silked significantly later than all check hybrids except Anjou 285, which silked significantly later than maize hybrid RPG824. The root lodging score for maize hybrid RPG824 was significantly higher than that for Twin, but was not significantly different than those of the other check hybrids. The harvest lodging percentage for maize hybrid RPG824 was significantly higher than those of Marignan and Fanion. The early vigor rating of maize hybrid RPG824 was significantly lower than that of Marignan and not significantly different than the other check hybrids. The plant height of maize hybrid RPG824 was significantly higher than all check hybrids, except Fanion.

Table 9 depicts the results of another set of private yield trials conducted at two locations in France in 1997. The mean harvest moisture and grain yield of maize hybrid RPG824 were significantly higher than those values of the three elite check hybrids. Maize hybrid RPG824 silked significantly later than the other checks and had a significantly lower root lodging score. The early vigor rating of maize hybrid RPG824 was significantly higher than that of Banguy, and not significantly different than those of the other check hybrids. Maize hybrid RPG824 was significantly taller than the other check hybrids.

Table 10 shows the average performance of maize hybrid RPG824 and two elite check hybrids in another series of private grain trials over six French locations in 1998. The grain moisture of maize hybrid RPG824 was significantly lower than that of Anjou 285. The average grain yield of RPG824 was significantly higher than either elite check hybrid. Maize hybrid RPG824 silked significantly later than Fanion, but significantly earlier than Anjou 285. The harvest lodging score of maize hybrid RPG824 was significantly lower than that of Fanion and the early vigor score was significantly higher than Anjou 285. The plant height of maize hybrid RPG824 was significantly higher than that of Fanion.

Table 11 depicts performance summaries of maize hybrid RPG824 and eighteen elite check varieties in another set of private grain trials summarized over four French locations in 1998. The grain moisture of maize hybrid RPG824 was significantly higher than that of Kerkenna and was significantly lower than those of the other check hybrids, except for those of Fanion and Romario. The grain yield of maize hybrid RPG824 was significantly higher than all check hybrids, except that of Romario. The silking date of maize hybrid RPG824 was significantly earlier than that of Oleron, was not significantly different from those of Acores, Spitzberg, and Anjou 285, and was significantly later than those of the other check hybrids. The harvest lodging percentage of maize hybrid RPG824 was significantly higher than those of Jersey, Djerba, Banguy, Fanion, Lopez, Vancouver, Anjou 258 and Romario, and was not significantly different than the other elite check hybrids. The harvest lodging rating of maize hybrid RPG824 was significantly higher than that of Kerkenna and significantly lower than those of Djerba, Banguy, Fanion, Lopez, and Anjou 258. The early vigor score of maize hybrid RPG824 was significantly higher than those of Fernando, Carrera, and Anjou 285 and was significantly lower than those of Spitzberg, Vancouver, and Magister. The average plant height of maize hybrid RPG824 was significantly higher than all other elite check hybrids.

TABLE 8

1997 FRENCH PRIVATE GRAIN TRIALS* (13 LOCATIONS)

| HYBRID | H2O (%) | sH2O | Yield (q/ha) | sYield | Yield (% CK) | Root Lodging (1–5) | Silk Date (Julian) | Harvest Lodging (%) | Harvest Lodging (1–5) | Early Vigor (1–5) | Plant Ht (cm) |
|---|---|---|---|---|---|---|---|---|---|---|---|
| ANJOU285 | 28.1 | 1.4 | 102.56 | 5.33 | 106 | 3.7 | 207 | 4 | 3.8 | 3.4 | 256 |
| DEA | 32.5 | 1.1 | 99.72 | 7.12 | 103 | 3.8 | 205 | 6 | 4.1 | 3.5 | 241 |
| FAN10N | 29.0 | 1.0 | 98.93 | 5.43 | 102 | 3.8 | 205 | 2 | 4.3 | 3.5 | 258 |
| TWIN | 30.0 | 0.8 | 98.86 | 11.77 | 102 | 3.3 | 205 | 4 | 4.0 | 3.5 | 244 |
| LG2244 | 28.3 | 1.6 | 97.75 | 8.99 | 101 | 3.8 | 205 | 6 | 4.1 | 3.3 | 239 |
| LG2243 | 28.6 | 0.6 | 89.79 | 7.80 | 93 | 3.7 | 205 | 9 | 3.8 | 3.6 | 253 |

TABLE 8-continued

1997 FRENCH PRIVATE GRAIN TRIALS*
(13 LOCATIONS)

| HYBRID | H2O (%) | sH2O | Yield (q/ha) | sYield | Yield (% CK) | Root Lodging (1–5) | Silk Date (Julian) | Harvest Lodging (%) | Harvest Lodging (1–5) | Early Vigor (1–5) | Plant Ht (cm) |
|---|---|---|---|---|---|---|---|---|---|---|---|
| MARIGNAN | 29.3 | 1.2 | 88.92 | 9.05 | 92 | 3.7 | 204 | 3 | 4.1 | 4.0 | 217 |
| RPG824 | 28.3 | 1.1 | 110.16 | 7.04 | 114 | 4.0 | 206 | 9 | 3.9 | 3.5 | 265 |
| MEAN | 30.4 | | 98.20 | | | 3.7 | 207 | 5 | 4.0 | 3.5 | 256 |
| LSD (.05) | 0.9 | | 6.71 | | | 0.4 | 1 | 6 | 0.5 | 0.4 | 9 |
| CV | 3.0 | | 6.83 | | | 12.2 | 1 | 121 | 11.8 | 12.0 | 3 |

*H2O, grain moisture at harvest;
Yield adjusted to 15.5% grain moisture basis;
sH2O, standard error-grain moisture at harvest, entry basis;
sYield, standard error, grain yield at harvest, entry basis; and
Visual (1–5) ratings, 1 = least preferred expression, 5 = most preferred expression, for trait.

TABLE 9

1997 FRENCH PRIVATE GRAIN TRIALS*
(2 LOCATIONS)

| HYBRID | H2O (%) | sH2O | Yield (q/ha) | sYield | Yield (% CK) | Silk Date (Julian) | Harvest Lodging (1–5) | Early Vigor (1–5) | Plant Ht (cm) |
|---|---|---|---|---|---|---|---|---|---|
| FANION | 36.0 | 0.6 | 95.15 | 4.82 | 108 | 217 | 5.0 | 3.3 | 263 |
| BANGLY | 36.2 | 0.5 | 85.78 | 4.26 | 97 | 211 | 4.8 | 3.0 | 234 |
| HELIX | 34.6 | 0.7 | 83.74 | 4.73 | 95 | 214 | 5.0 | 3.3 | 269 |
| RPG824 | 37.5 | 0.0 | 110.24 | 0.75 | 125 | 218 | 4.2 | 3.3 | 283 |
| MEAN | 36.4 | | 92.73 | | | 216 | 4.9 | 3.1 | 253 |
| LSD (.05) | 0.8 | | 6.59 | | | 1 | 0.2 | 0.3 | 7 |
| CV | 2.3 | | 7.11 | | | 0 | 5.1 | 10.1 | 3 |

*H2O, grain moisture at harvest;
sH2O, standard error-grain moisture at harvest, entry basis;
Yield adjusted to 15.5% grain moisture basis;
sYield, standard error, grain yield at harvest, entry basis;
Visual (1–5) ratings, 1 = least preferred expression, 5 = most preferred expression, for trait;
Harvest Lodging, visual (1–5) rating of harvest lodging, 1 = least preferred expression, 9 = most preferred expression, for trait; and
Early Vigor, visual rating for early vigor, 1 = least preferred expression, 9 = most preferred expression, for trait.

TABLE 10

1998 FRENCH PRIVATE GRAIN TRIALS*
(6 LOCATIONS)

| HYBRID | H2O (%) | sH2O | Yield (q/ha) | sYield | Yield (% CK) | Silk Date (Julian) | Broken Stalks (%) | Harvest Lodging (1–5) | Early Vigor (1–5) | Plant Ht (cm) |
|---|---|---|---|---|---|---|---|---|---|---|
| ANJOU285 | 36.8 | 1.2 | 87.85 | 6.72 | 100 | 208 | 0 | 4.0 | 2.7 | 220 |
| FANION | 35.0 | 0.8 | 87.64 | 8.63 | 100 | 204 | 0 | 4.7 | 3.7 | 210 |
| RPG824 | 34.9 | 1.1 | 97.56 | 4.73 | 111 | 206 | 0 | 3.9 | 3.5 | 223 |
| MEAN | 36.2 | | 86.4 | | | 205 | 10 | 4.3 | 3.3 | 201 |
| LSD (.05) | 1.0 | | 8.27 | | | 2 | 13 | 0.4 | 0.5 | 8 |
| CV | 2.7 | | 9.57 | | | 1 | 129 | 8.7 | 14.6 | 4 |

*H2O, grain moisture at harvest;
sH2O, standard error-grain moisture at harvest, entry basis;
Yield adjusted to 15.5% grain moisture basis;
sYield, standard error, grain yield at harvest, entry basis;
Harvest Lodging, visual (1–5) rating of harvest lodging, 1 = least preferred expression, 9 = most preferred expression, for trait; and
Early Vigor, visual rating for early vigor, 1 = least preferred expression, 9 = most preferred expression, for trait.

TABLE 11

1998 FRENCH PRIVATE GRAIN TRIALS*
(4 LOCATIONS)

| HYBRID | H2O (%) | sH2O | Yield (q/ha) | sYield | Yield (% CK) | Silk Date (Julian) | Harvest Lodging (%) | Harvest Lodging (1–5) | Early Vigor (1–5) | Plant Ht (cm) |
|---|---|---|---|---|---|---|---|---|---|---|
| ROMARIO | 34.4 | 0.4 | 114.11 | 5.50 | 112 | 205 | 7 | 4.4 | 3.8 | 252 |
| MAGISTER | 37.2 | 0.6 | 107.07 | 4.08 | 105 | 206 | 14 | 4.0 | 4.0 | 250 |
| ANJOU258 | 37.3 | 0.2 | 104.61 | 3.12 | 102 | 206 | 3 | 4.9 | 3.8 | 260 |
| VANCOUVER | 36.0 | 1.1 | 104.13 | 2.38 | 102 | 206 | 7 | 4.0 | 4.0 | 245 |
| ANJOU285 | 38.0 | | 101.83 | | 100 | 207 | | 4.0 | 3.0 | 256 |
| LOPEZ | 35.3 | 1.0 | 100.13 | 3.12 | 98 | 204 | 2 | 4.9 | 3.3 | 244 |
| CARRERA | 37.4 | 0.6 | 99.53 | 3.73 | 97 | 206 | 11 | 4.4 | 3.0 | 264 |
| FANION | 33.7 | 1.3 | 99.04 | 9.78 | 97 | 205 | 5 | 4.6 | 3.8 | 238 |
| BANGUY | 37.1 | 1.1 | 98.28 | 4.40 | 96 | 203 | 8 | 4.6 | 3.5 | 240 |
| DJERBA | 36.5 | 0.7 | 97.89 | 2.13 | 96 | 206 | 4 | 4.6 | 3.5 | 263 |
| LORENZO | 36.0 | 1.0 | 97.36 | 2.95 | 95 | 205 | 12 | 4.4 | 3.5 | 253 |
| OTTO | 35.5 | 0.8 | 97.36 | 3.80 | 95 | 206 | 9 | 4.4 | 3.8 | 248 |
| SPITZBERG | 36.3 | 0.9 | 97.15 | 7.98 | 95 | 207 | 13 | 4.3 | 4.0 | 264 |
| ACORES | 37.2 | 0.8 | 96.43 | 7.48 | 94 | 207 | 12 | 4.3 | 3.5 | 250 |
| KERKENNA | 33.5 | 0.6 | 95.76 | 11.09 | 94 | 206 | 19 | 2.8 | 3.3 | 256 |
| JERSEY | 37.4 | 0.7 | 94.26 | 4.12 | 92 | 206 | 5 | 4.4 | 3.5 | 261 |
| FERNANDO | 36.0 | 0.6 | 93.98 | 11.14 | 92 | 206 | 12 | 4.3 | 2.3 | 266 |
| OLERON | 36.4 | 0.6 | 87.42 | 5.81 | 85 | 208 | 16 | 4.1 | 3.8 | 271 |
| RPG824 | 34.1 | 1.2 | 118.11 | 8.60 | 116 | 207 | 14 | 4.1 | 3.5 | 280 |
| MEAN | 36.2 | | 99.16 | | | 206 | 11 | 4.3 | 3.5 | 257 |
| LSD (.05) | 0.5 | | 5.24 | | | 1 | 6 | 0.4 | 0.4 | 8 |
| CV | 1.5 | | 5.28 | | | 1 | 56 | 10.5 | 12.4 | 3 |

*H2O, grain moisture at harvest;
Yield adjusted to 15.5% grain moisture basis;
sH2O, standard error-grain moisture at harvest, entry basis;
sYield, standard error, grain yield at harvest, entry basis; and
Visual (1–5) ratings, 1 = least preferred expression, 5 = most preferred expression, for trait.

EXAMPLE 4

Performance of Maize Hybrid RPG824 in Private Austrian Trials

Table 12 summarizes the results of grain trials conducted at four Austrian locations in 1997. The harvest moisture of maize hybrid RPG824 was significantly lower than that of DK300 and not significantly different than the other check hybrids. However, the grain yield of RPG824 was significantly higher than that of any check hybrid. Root lodging and harvest lodging scores of maize hybrid RPG824 were similar to those of the elite check hybrids, except the harvest lodging score of RPG824 was significantly higher than that of the check hybrid JERSEY.

TABLE 12

1997 AUSTRIAN PRIVATE GRAIN TRIALS*
(4 LOCATIONS, 3 REPLICATIONS/LOCATION)

| HYBRID | H20 (%) | sH20 | Yield (q/ha) | sYield | Root Lodging (1–5) | Harvest Lodging (1–5) |
|---|---|---|---|---|---|---|
| VANCOUVER | 27.0 | 0.8 | 139.04 | 4.37 | 4.7 | 4.0 |
| DK300 | 31.3 | 0.8 | 135.71 | 4.72 | 4.5 | 3.7 |
| SPITZBERG | 26.6 | 1.2 | 135.42 | 5.01 | 4.8 | 4.0 |
| JERSEY | 25.8 | 0.2 | 134.54 | 10.97 | 4.8 | 3.3 |
| ANJOU285 | 26.4 | 1.7 | 134.47 | 6.58 | 4.6 | 4.0 |
| ACORES | 26.9 | 0.9 | 132.77 | 6.73 | 4.6 | 3.5 |
| FANION | 25.4 | 1.3 | 131.32 | 5.65 | 4.8 | 3.5 |
| RPG824 | 25.3 | 0.9 | 155.74 | 9.18 | 4.6 | 4.0 |
| TRIAL MEAN | 27.0 | | 134.1 | | 4.6 | 3.6 |
| LSD(.05) | 1.8 | | 15.5 | | 0.3 | 0.6 |
| CV | 4 | | 5.9 | | 9.3 | 9.5 |

*H20, grain moisture at harvest;
Yield adjusted to 15.5% grain moisture basis;
sH20, standard error-grain moisture at harvest, entry basis;

TABLE 12-continued

1997 AUSTRIAN PRIVATE GRAIN TRIALS*
(4 LOCATIONS, 3 REPLICATIONS/LOCATION)

| HYBRID | H20 (%) | sH20 | Yield (q/ha) | sYield | Root Lodging (1–5) | Harvest Lodging (1–5) |
|---|---|---|---|---|---|---| sYield, standard error, grain yield at harvest, entry basis; and
Visual (1–5) ratings, 1 = least preferred expression, 5 = most preferred expression, for trait.

EXAMPLE 5

Performance of Maize Hybrid RPG824 in Official French Grain Trials

Table 13 depicts summaries of maize hybrid RPG824 and elite check hybrids in the 1998 official French grain trials. The average grain yield of maize hybrid RPG824 was significantly higher than that of any check. The average grain moisture of RPG824 was significantly lower than that of Anjou 285 and not significantly different than the others. The early vigor score of maize hybrid RPG824 was lower than that of LG 2243 and Fanion and was higher than those of the other check hybrids. The average flowering date of maize hybrid RPG824 was later than those of LG 2243, Fanion, and DK 250 and earlier than that of Anjou 285. Percentage stalk breakage at harvest for maize hybrid RPG824 was higher than those of the other elite check hybrids. Percentage smutted plants for maize hybrid RPG824 was about the same as that for LG 2244 and higher than those for the other check hybrids.

TABLE 13

1998 OFFICIAL FRENCH GRAIN TRIALS*
(10 LOCATIONS, 3 REPLICATIONS/LOCATION)

| Variety | Yield (q/ha) | Yield (% Check) | Moisture (%) | Early Vigor (1–5) | Flowering Date (Julian) | Stalk Breakage at Harvest Time (%) | SMUT (%) |
|---|---|---|---|---|---|---|---|
| DK 250 | 101.3 | 92.1 | 32.6 | 3.2 | 200.0 | 5.4 | 1.7 |
| Fanion(ck) | 107.6 | 98.0 | 32.0 | 3.7 | 201.1 | 3.0 | 4.0 |
| Anjou 285(ck) | 112.0 | 102.0 | 34.2 | 3.1 | 204.3 | 7.9 | 4.0 |
| LG 2244(ck) | 107.8 | 98.2 | 32.7 | 3.3 | 201.6 | 6.5 | 9.0 |
| LG 2243 | 104.0 | 94.8 | 32.8 | 3.7 | 200.6 | 2.5 | 7.0 |
| Prinz | 111.1 | 102.1 | 32.6 | 3.4 | 202.0 | 7.2 | 5.7 |
| RPG824 | 121.3 | 110.2 | 32.5 | 3.5 | 201.9 | 23.4 | 10.7 |
| Trial Mean | 109.6 | 100.0 | 33.1 | 3.4 | 202.9 | 5.4 | 4.0 |
| LSD(.05) | 2.4 | — | 0.9 | — | — | 7.9 | — |
| CV | 6.2 | — | 2.7 | — | — | — | — |
| Locations | 10 | 10 | 10 | 3 | 5 | 3 | 1 |

*Yield adjusted to 15.5% grain moisture basis;
Moisture, grain moisture at harvest;
Visual (1–5) ratings, 1 = least preferred expression, 5 = most preferred expression, for trait;
Smut measures % plants infected by common smut (*Ustilago maydis*);
(ck) indicates official check variety

EXAMPLE 6
Performance of Maize Hybrid RPG824 in Official German Grain Trials Table 14 summarizes the results of the 1998 official German grain trials. Maize hybrid RPG824 flowered later than the other check hybrids and was taller, except for Galice. Percentage broken stalks at harvest for RPG824 was lower than those of Fernando and Galice and higher than those of the other check hybrids. The root lodging score for maize hybrid RPG824 was lower than those of Galice, Symphony, Lenz and Harpun and was similar to those of the other check hybrids. The Fusarium score for maize hybrid RPG824 was lower than those for Symphony, Probat, Attribut, Santiago, and Lenz, was equal to that of Turkus, and was higher than those of the other check hybrids. The percentage smutted plants of maize hybrid RPG824 was higher than those of Symphony and Probat, equal to those of Fernando and Attribut, and was lower than those of the other check hybrids. The percentage of Maize Hybrid RPG824 plants infested by European Corn Borer was equal to those of Symphony, Probat, and Turkus and was higher than those of the other check hybrids. The grain yield of maize hybrid RPG824 was significantly higher than those of the other check hybrids, while the grain moisture of maize hybrid RPG824 was significantly lower than that of Symphony, significantly higher than those of Fernando, Galice, Probat, and Attribut, and was equal to those of the other check hybrids.

TABLE 14

1998 OFFICIAL GERMAN GRAIN TRIALS*

| No. Locations | Emergence Date 15 | Flowering Date 12 | Plant Height (cm) 14 | Broken Stalks at Harvest (%) 11 | Root Lodging (%) 1 | Tillers/Plant 4 | Fusarium (1–5) 7 | SMUT (%) 7 | Corn Borer (%) 5 | Yield (q/ha) 15 | Yield (% checks) 15 | Moisture (%) 15 | Weight 1000 Kernels (g) 7 | Broken Kernels (%) 7 |
|---|---|---|---|---|---|---|---|---|---|---|---|---|---|---|
| HARPUN | 10.05.98 | 10.07.98 | 256 | 3 | 1.8 | 1.3 | 1.4 | 4 | 7 | 103.2 | 95 | 69.2 | 310.3 | 2.2 |
| TÜRKUS | 10.05.98 | 10.07.98 | 256 | 7 | 1.0 | 16. | 1.9 | 4 | 9 | 109.0 | 101 | 69.6 | 281.1 | 2.0 |
| LENZ | 11.05.98 | 09.07.98 | 247 | 6 | 4.0 | 1.1 | 2.3 | 4 | 4 | 112.5 | 104 | 69.7 | 310.9 | 2.0 |
| Check Avg. | 10.05.98 | 10.07.98 | 253 | 5 | 2.3 | 1.3 | 1.8 | 4 | 7 | 108.2 | 108 | 69.5 | 300.8 | 2.1 |
| SANTIAGO | 10.05.98 | 10.07.98 | 232 | 7 | 1.0 | 1.4 | 2.3 | 6 | 7 | 104.0 | 96 | 69.3 | 326.2 | 2.8 |
| PRINZ | 10.05.98 | 09.07.98 | 247 | 3 | 1.0 | 1.0 | 1.6 | 5 | 8 | 113.4 | 105 | 69.8 | 273.0 | 1.4 |
| ATTRIBUT | 10.05.98 | 11.07.98 | 262 | 2 | 1.0 | 1.0 | 2.1 | 3 | 4 | 111.9 | 103 | 67.4 | 300.3 | 1.8 |
| PROBAT | 11.05.98 | 10.07.98 | 254 | 7 | 1.0 | 1.1 | 3.2 | 1 | 9 | 112.7 | 104 | 68.4 | 259.4 | 2.4 |
| SYMPHONY | 11.05.98 | 09.07.98 | 246 | 5 | 1.3 | 2.9 | 2.1 | 2 | 9 | 107.8 | 100 | 70.7 | 276.9 | 2.1 |
| GALICE | 11.05.98 | 11.07.98 | 273 | 10 | 2.8 | 2.4 | 1.4 | 11 | 7 | 111.8 | 103 | 67.7 | 345.3 | 3.2 |
| FERNANDO | 10.05.98 | 12.07.98 | 264 | 13 | 1.0 | 3.7 | 1.2 | 3 | 8 | 115.7 | 107 | 68.6 | 283.6 | 4.2 |
| RPG824 | 10.05.98 | 15.07.98 | 270 | 9 | 1.0 | 1.1 | 1.9 | 3 | 9 | 120.8 | 112 | 69.7 | 296.9 | 1.6 |
| Mean | 10.05.98 | 11.07.98 | 256 | 7 | 1.3 | 1.6 | 9.2 | 4 | 8 | 110.7 | 102 | 58.9 | 291.6 | 2.5 |
| LSD(.05) | — | — | — | — | — | — | — | — | — | 5.1 | 4.8 | 1.0 | — | — |
| CV | — | — | — | — | — | — | — | — | — | 5.6 | 5.2 | 3.8 | — | — |

*Root lodging, % plants tilted greater than or equal to 15° from vertical;
Fusarium, visual rating of Fusarium stalk rot (*Fusarium moniliforme*), 1 = least preferred expression, 5 + most preferred expression, for trait;
Smut, % plants infected by common smut (*Ustilago maydis*);
Corn borer, % plants infected by 2d Brood European Corn Borer (*Ostrinia nubilalis*); and
Yield adjusted to 15.5% grain moisture basis.

EXAMPLE 7
Performance of Maize Hybrid RPG824 in Official Austrian Grain Trials Table 15 depicts a summary of the 1998 official Austrian grain trials. In this series of trials, grain yields were reported as percentages of the average of the check hybrids. The percent yield of RPG824 was significantly higher than those of Anjou 228, Anjou 246, and LG 22.75 and not significantly different than the others. Maize hybrid RPG824 had a higher percentage of broken stalks at harvest and a lower grain moisture than the check hybrids.

was significantly lower than those of Kallista and Frivol and was significantly higher than that of Monopol. Plant and ear heights of maize hybrid RPG824 were significantly higher than those of the other elite check hybrids. The grain yield of maize hybrid RPG824 was significantly higher than those of the other check hybrids and the harvest moisture of maize hybrid RPG824 was significantly lower. The percent smutted plants of maize hybrid RPG824 was significantly lower than that of Monopol. The ratio of ear height to plant height

TABLE 15

1998 OFFICIAL AUSTRIAN GRAIN TRIALS*

| | 9 | 1 | 2 | 3 | 4 | 5 | 6 | 7 | 8 | % Yield/ Average | N | Broken Plants at Harvest(%) Mean | N | Grain Moisture(%) MIT | N |
|---|---|---|---|---|---|---|---|---|---|---|---|---|---|---|---|
| Location | WUL | RIT | ST. | EPE | MAR | PAS | GLE | MOO | JAK | Mean | | Mean | | MIT | |
| ROMARIO(%) | 115 | 108 | 104 | 104 | 108 | 103 | 106 | 101 | 102 | 106 | 9 | 6.7 | 8 | 29.5 | 9 |
| TRENTO(%) | 105 | 101 | 113 | 101 | 95 | 99 | 99 | 111 | 103 | 103 | 9 | 4.6 | 8 | 30.7 | 9 |
| PROBAT(%) | 111 | 98 | 107 | 95 | 98 | 100 | 99 | 109 | 104 | 103 | 9 | 7.1 | 8 | 30.3 | 9 |
| LG 22.75(%) | 100 | 97 | 97 | 95 | 106 | 94 | 98 | 114 | 107 | 101 | 9 | 3.7 | 8 | 31.5 | 9 |
| ANJOU 246(%) | 101 | 98 | 98 | 99 | 108 | 96 | 95 | 103 | 106 | 101 | 9 | 4.9 | 8 | 31.3 | 9 |
| ANJOU 228(%) | 101 | 95 | 97 | 97 | 102 | 101 | 83 | 88 | 105 | 96 | 9 | 2.1 | 8 | 29.3 | 9 |
| RPG824(%) | 112 | 112 | 107 | 105 | 117 | 107 | 103 | 102 | 114 | 109 | 9 | 8.6 | 8 | 28.7 | 9 |
| Mean(q/ha) | 112 | 128 | 115 | 127 | 120 | 131 | 133 | 116 | 129 | 123 | — | — | — | — | — |
| LSD(.05) | 7 | 6 | 9 | 8 | 7 | 8 | 9 | 10 | 7 | 7.8 | — | — | — | — | — |
| CV | 4.5 | 3.4 | 5.6 | 4.5 | 6.2 | 6.6 | 4.9 | 6.2 | 3.9 | 4.6 | — | — | — | — | — |

*Percent grain yield of check average

EXAMPLE 8
Performance of Maize Hybrid RPG824 in 1998 Official Swiss Grain Trials Table 16 summarizes the results of the 1998 official Swiss grain trials. The early vigor score of maize hybrid RPG824 of maize hybrid RPG824 was significantly higher than those of the other check varieties. The flowering date of hybrid RPG824 was significantly later than those of LG 2227, LG 2243, Frivol, and Monopol and not significantly different from the others.

TABLE 16

1998 OFFICIAL SWISS GRAIN TRIALS*

| | Stalk Fusarium Index | Average Index | Early Vigor (1–5) | Plant Height (cm) | Ear Height (cm) | Broken Plants (1–5) | Shelling Ability (1–5) | Yield (q/ha) | Yield (% Check Mean) | Moisture (%) |
|---|---|---|---|---|---|---|---|---|---|---|
| Monopol | 0.02 | 0.83 | 2.2 | 238 | 102 | 1.1 | 1.9 | 123.9 | 99.9 | 69.7 |
| LG 22.40 | −0.02 | −0.83 | 3.3 | 237 | 104 | 1.7 | 1.0 | 124.2 | 100.1 | 69.5 |
| Frivol | −0.68 | −9.26 | 3.8 | 210 | 89 | 1.3 | 1.9 | 114.6 | 92.4 | 69.6 |
| LG 22.43 | −0.92 | 4.53 | 2.8 | 223 | 97 | 2.0 | 0.9 | 122.2 | 98.5 | 69.0 |
| Kallista | −0.82 | −2.00 | 4.1 | 227 | 96 | 1.8 | 1.3 | 122.9 | 99.1 | 70.1 |
| LG 22.27 | −0.64 | −1.10 | 3.1 | 233 | 102 | 1.6 | 1.1 | 121.5 | 98.0 | 70.4 |
| RPG824 | −0.39 | 13.62 | 3.1 | 283 | 132 | 2.0 | 1.3 | 146.3 | 117.9 | 68.5 |
| CV | | | 2.4 | 3 | 4 | 49.5 | 44.6 | 5.3 | | 0.9 |
| LSD(.05) | | | 0.4 | .2 | 8 | | 0.5 | 4.0 | | 0.4 |

| | Root Lodging(%) | Lodging at Harvest(%) | Broken Plants(%) | SMUT (%) | Fusarium (%) | Plants/m$^2$ | Ear Height/ Plant Height(%) | Flowering(Female) (Days From Planting) |
|---|---|---|---|---|---|---|---|---|
| Monopol | 5.6 | 0.1 | 1.2 | 11.2 | 1.6 | 9.4 | 43.0 | 72.7 |
| LG 22.40 | 1.1 | 0.1 | 2.2 | 2.5 | 1.2 | 9.5 | 43.9 | 73.2 |
| Frivol | 2.2 | 0.3 | 1.1 | 4.5 | 4.4 | 9.3 | 42.7 | 72.3 |
| LG 22.43 | 1.4 | 0.3 | 3.7 | 2.2 | 5.4 | 9.5 | 43.6 | 72.5 |
| Kallista | 2.8 | 0.1 | 2.4 | 2.7 | 5.0 | 9.5 | 42.2 | 74.6 |
| LG 22.27 | 1.4 | 0.2 | 2.4 | 2.3 | 4.2 | 9.6 | 43.7 | 72.8 |
| RPG824 | 4.2 | 0.4 | 3.6 | 0.3 | 3.3 | 9.6 | 47.0 | 74.2 |
| CV | 88.5 | 293.2 | 172.2 | 110.6 | 77.9 | 2.8 | 4.1 | 1.1 |
| LSD(.05) | 3.6 | 0.6 | 3.6 | 4.5 | 2.9 | 0.2 | 3.1 | 1.4 |

*Yield, adjusted to a 15.5% grain moisture basis;
Root lodging, % plants tilted greater than or equal to 15°;
Broken plants, % plants broken below the ear at harvest;
Smut, % plants infected with common smut (*Ustilago maydis*);
Fusarium, % plants infected with Fusarium stalk rot (*Fusarium moniliforme*); and
Visual ratings, lowest number = least preferred expression, highest number = most preferred expression, for the trait.

EXAMPLE 9

Performance of Maize Hybrid RPG824 in The Netherlands Official Grain Trials

Table 17 shows summarized results of the Netherlands 1998 official grain trials. The early vigor rating for maize hybrid RPG824 was higher than those of LG 2184, DK 210, and Kallista and was lower than those of the other check hybrids. The harvestability rating for maize hybrid RPG824 was higher than those of DK 210, Menno, and Pongo and was lower than the other check hybrids. The ease of shelling rating for maize hybrid RPG824 was lower than those of Manatan and Husar and was higher than those of the other check hybrids. Plant and ear heights of maize hybrid RPG824 were higher than those of the check hybrids. Grain dry matter percent of maize hybrid RPG824 was higher than those of LG 2184, Kallista, and Pongo, equal to those of DK 210 and Fanion, and less than those of the other check hybrids. The grain yield of maize hybrid RPG824 was significantly lower than that of Symphony., equal to that of DK210, and significantly higher than those of the other check hybrids.

EXAMPLE 10

Performance of Maize Hybrid RPG824 in French Private Silage Trials

Table 18 depicts summarized results of private silage trials conducted at six French locations in 1997. The stover yield of maize hybrid RPG824 was significantly higher than those of the other elite checks and the root lodging score of maize hybrid RPG824 was significantly lower. The plant height of maize hybrid RPG824 was significantly higher than those of Marignan, LG 2243, Banguy, and Anjou 285 and significantly lower than that of Anjou 265. The estimate for energy available for milk production for RPG824 was significantly higher than the estimate for Anjou 285 and was significantly lower than the estimate for Fanion. The digestibility estimate for maize hybrid RPG824 was significantly higher than the estimate for Anjou 285 and significantly lower than that for Fanion.

TABLE 17

THE NETHERLANDS 1998 OFFICIAL GRAIN TRIALS*

|  | Plants Emerged (%) | Early Vigor (Rating) | Harvest-ability (Rating) | Ease of Shelling (Rating) | Plant Height (% Checks) | Ear Height (% Checks) | Dry Matter (% Checks) | Yield (% Checks) |
|---|---|---|---|---|---|---|---|---|
| Fanion | 94 | 6.5 | 8.5 | 7.6 | 105 | 108 | 99 | 97 |
| Pongo | 94 | 6.6 | 5.2 | 6.6 | 103 | 103 | 97 | 99 |
| Menno | 97 | 6.8 | 5.1 | 7.2 | 103 | 102 | 100 | 99 |
| Symphony | 99 | 6.5 | 8.3 | 7.6 | 98 | 90 | 101 | 108 |
| Husar | 97 | 7.5 | 8.6 | 8.1 | 101 | 99 | 105 | 95 |
| Kallista | 97 | 5.0 | 8.7 | 6.7 | 104 | 96 | 97 | 98 |
| Manatan | 94 | 7.6 | 8.6 | 7.9 | 89 | 101 | 102 | 96 |
| DK 210 | 85 | 5.4 | 3.4 | 6.6 | 100 | 97 | 99 | 106 |
| LG 21.84 | 95 | 5.0 | 8.4 | 5.6 | 99 | 99 | 98 | 101 |
| RPG824 | 97 | 5.8 | 5.6 | 7.8 | 118 | 116 | 99 | 104 |
| MEAN | — | — | — | — | 246(cm) | 94(cm) | 66.5(%) | 92(q/ha) |
| CV | — | — | — | — | — | — | 1.1 | 4.0 |
| LSD(.05) | — | — | — | — | — | — | 0.5 | 2.5 |

*Ratings, lowest number = least preferred expression, highest number = most preferred expression, for the trait;
Dry matter, dry matter of grain at harvest as % check mean; and
Yield adjusted to 15.5% grain moisture basis and expressed as % check mean.

TABLE 18

1997 FRENCH PRIVATE SILAGE TRIALS*
(6 LOCATIONS)

|  | Dry Matter (%) | Stover (t/ha) | Root Lodging (1–5) | Harvest Lodging (%) | Early Vigor (1–5) | Plant Height (cm) | Units Available Milk Production (Ratio)(UFL) | Digestibility (DMO) | Starch (%)(AMI) |
|---|---|---|---|---|---|---|---|---|---|
| ANJOU285 | 31.0 | 16.3 | 3.5 | −0 | 3.8 | 265 | 0.931 | 73.21 | 26.49 |
| ANJOU265 | 30.9 | 16.3 | 5.0 | −0 | 4.0 | 290 |  |  |  |
| BEMOL | 32.6 | 15.8 | 4.5 | −0 | 4.0 | 280 | 0.940 | 73.61 | 28.10 |
| FANION | 31.8 | 15.0 | 5.0 | −0 | 3.9 | 270 | 0.962 | 74.92 | 27.57 |
| BANGUY | 32.3 | 14.4 | 4.0 | −0 | 3.9 | 240 |  |  |  |
| LG2243 | 32.3 | 14.3 | 4.0 | −0 | 3.6 | 260 | 0.957 | 74.54 | 29.28 |
| MARIGNAN | 31.3 | 13.5 | 5.0 | −0 | 4.1 | 205 |  |  |  |
| RPG824 | 31.3 | 17.7 | 1.5 | −0 | 3.9 | 275 | 0.948 | 74.17 | 27.70 |
| MEAN | 30.9 | 15.4 | 3.7 | 1 | 3.7 | 267 | 0.950 | 74.23 | 28.06 |
| LSD(.05) | 1.2 | 1.2 | 0.7 | 4 | 0.4 | 10 | 0.014 | 0.74 | 2.22 |
| CV | 3.8 | 7.8 | 18.6 | 563 | 12.2 | 4 | 1.488 | 0.99 | 7.91 |

*Visual ratings, lowest number = least preferred expression, highest number = most preferred expression, for trait.

EXAMPLE 11
Performance of Maize Hybrid RPG824 in German Private Silage Trials Table 19 summarizes the results of private silage trials conducted at one location in Germany in 1997. The stover yield estimate for maize hybrid RPG824 was significantly higher than those of the check hybrids. The early vigor score for maize hybrid RPG824 was significantly lower than those for Banguy and Helix. The flowering date of maize hybrid RPG824 was significantly later than those of the check hybrids and the plant height of RPG824 was significantly higher.

TABLE 19

| | Dry Matter (%) | Stover (t/ha) | Root Lodging (1–5) | Early Vigor (1–5) | Flowering (Julian) | Plant Height (cm) |
|---|---|---|---|---|---|---|
| FANION | 38.1 | 15.2 | 5.0 | 3.3 | 210 | 245 |
| HELIX | 37.9 | 14.8 | 5.0 | 3.5 | 209 | 253 |
| BANGUY | 38.3 | 14.5 | 5.0 | 3.7 | 207 | 230 |
| RPG824 | 38.1 | 19.4 | 5.0 | 3.0 | 212 | 273 |
| MEAN | 37.4 | 15.7 | 5.0 | 3.3 | 211 | 250 |
| LSD(.05) | 0.9 | 0.6 | 0.0 | 0.4 | 1 | 7 |
| CV | 2.5 | 3.8 | 0.0 | 11.6 | 1 | 3 |

1997 GERMAN PRIVATE SILAGE TRIALS* (1 LOCATION)

*Visual ratings, lowest number = least preferred expression, highest number = most preferred expression, for trait.

EXAMPLE 12
Performance of Maize Hybrid RPG824 in Belgian Private Silage Trials Table 20 summarizes the performance of maize hybrid RPG824 in silage trials at three Belgian locations in 1997. With the exception of LG 2243, the percent dry matter of hybrid RPG824 was significantly higher than those of the other check hybrids. Stover yields of maize hybrid RPG824 were significantly higher than those of the other check hybrids. The digestibilities for maize hybrid RPG824 were significantly lower than those for LG 2243 and Banguy and the starch percentage estimate was significantly lower than that for Banguy.

TABLE 20

1997 BELGIAN PRIVATE SILAGE TRIALS* (3 LOCATIONS)

| | Dry Matter (%) | Stover (t/ha) | Digestibility (DMO) | Starch (%) AMI |
|---|---|---|---|---|
| FANION | 33.1 | 20.7 | 80.53 | 18.41 |
| LG2252 | 34.3 | 20.0 | 79.74 | 17.30 |
| BANGUY | 34.2 | 19.5 | 82.64 | 19.21 |
| LG2243 | 35.7 | 19.2 | 80.92 | 17.70 |
| SYMPHONY | 34.0 | 18.6 | 80.91 | 18.10 |
| RPG824 | 35.4 | 24.7 | 79.84 | 18.07 |
| MEAN | 35.0 | 20.5 | 80.29 | 18.08 |
| LSD (.05) | 0.9 | 0.9 | 1.08 | 0.88 |
| CV | 2.5 | 4.2 | 1.34 | 4.87 |

EXAMPLE 13
Performance of Maize Hybrid RPG824 in German Private Silage Trials Table 21 depicts summaries of private German silage trials conducted at two locations in 1998. The dry matter percentage estimate for maize hybrid RPG824 was significantly higher than those for Jersey, Fernando, Carrera, Fanion, Vancouver, Oleron, Magister, and Spitzberg and significantly lower than those for Djerba, Lopez, and Kerkenna. The stover yield estimate for maize hybrid RPG824 was not significantly different from that of Romario and was significantly higher than those for the other check hybrids. The root lodging score for maize hybrid RPG824 was significantly higher than that of only Fernando. The harvest lodging score for maize hybrid RPG824 was significantly higher than those for Fernando, Acoris, and Carrera. The early vigor rating for maize hybrid RPG824 was significantly higher than that for Jersey, was not significantly different from those of Anjou 258, Djerba, Carrera, Banguy, Acordis, and Fernando, and was significantly lower than the other check hybrids. The flowering date for maize hybrid RPG824 was significantly later than those of Romario, Lopez, Djerba, Fanion, and Banguy, significantly earlier than those of Vancouver, Carrera, and Fernando, and not significantly different than the other check hybrids. The plant height of maize hybrid RPG824 was not significantly different from that of Djerba, but was significantly greater than those of the other check hybrids. The digestibility estimate for maize hybrid RPG824 was significantly lower than those for Anjou 258, Spitzberg, Otto, Magister, Vancouver, Lorenzo, Fanion, and Banguy and was not significantly different than those of the other check hybrids. The percentage starch estimate for maize hybrid RPG824 was significantly lower than those for Lopez, Otto, Magister, and Lorenzo and was not significantly different than the other check hybrids.

TABLE 21

1998 GERMAN PRIVATE SILAGE TRIALS* (2 LOCATIONS)

| | Dry Matter (%) | Stover (t/ha) | Root Lodging (1–5) | Harvest Lodging (%) | Early Vigor (1–5) | Flowering (Julian) | Plant Height (cm) | Digestibility (DMO) | Starch (%)(AMI) |
|---|---|---|---|---|---|---|---|---|---|
| ROMARIO | 35.3 | 19.9 | 5.0 | 5.0 | 3.5 | 206 | 266 | 68.78 | 30.09 |
| ANJOU258 | 34.2 | 18.6 | 5.0 | 5.0 | 3 0 | 207 | 268 | 69.12 | 28.85 |
| SPITZBERG | 33.7 | 18.3 | 5.0 | 5.0 | 4.0 | 207 | 265 | 70.06 | 29.18 |
| KERKENNA | 38.6 | 18.3 | 5.0 | 5.0 | 3.3 | 207 | 271 | 68.09 | 31.08 |
| LOPEZ | 36.8 | 17.9 | 5.0 | 5.0 | 4.0 | 205 | 253 | 69.08 | 33.61 |
| OTTO | 34.7 | 17.8 | 5.0 | 5.0 | 3.3 | 207 | 263 | 70.81 | 35.04 |

TABLE 21-continued

1998 GERMAN PRIVATE SILAGE TRIALS*
(2 LOCATIONS)

|  | Dry Matter (%) | Stover (t/ha) | Root Lodging (1–5) | Harvest Lodging (%) | Early Vigor (1–5) | Flowering (Julian) | Plant Height (cm) | Digestibility (DMO) | Starch (%)(AMI) |
|---|---|---|---|---|---|---|---|---|---|
| MAGISTER | 32.9 | 17.6 | 5.0 | 5.0 | 4.0 | 207 | 260 | 70.93 | 33.21 |
| DJERBA | 36.2 | 17.5 | 5.0 | 5.0 | 3.0 | 206 | 275 | 66.66 | 28.80 |
| OLERON | 33.8 | 17.3 | 5.0 | 5.0 | 4.0 | 207 | 265 | 66.91 | 28.22 |
| VANCOUVER | 32.6 | 17.2 | 5.0 | 5.0 | 3.8 | 208 | 256 | 69.35 | 29.65 |
| LORENZO | 34.9 | 17.1 | 5.0 | 5.0 | 3.5 | 207 | 256 | 70.53 | 32.87 |
| FANION | 33.0 | 17.0 | 5.0 | 5.0 | 3.5 | 205 | 248 | 69.43 | 30.68 |
| CARRERA | 33.8 | 16.9 | 5.0 | 4.5 | 2.8 | 208 | 263 | 68.01 | 29.45 |
| BANGUY | 34.3 | 16.9 | 5.0 | 5.0 | 3.0 | 205 | 246 | 70.17 | 31.26 |
| ACORIS | 34.3 | 16.7 | 5.0 | 4.7 | 3.0 | 207 | 253 | 67.06 | 30.40 |
| FERNANDO | 32.9 | 16.7 | 4.5 | 3.5 | 3.0 | 208 | 264 | 68.42 | 29.10 |
| JERSEY | 33.5 | 15.5 | 5.0 | 5.0 | 2.3 | 207 | 264 | 68.42 | 30.96 |
| RPG824 | 34.9 | 19.8 | 5.0 | 5.0 | 2.8 | 207 | 279 | 67.54 | 29.98 |
| MEAN | 34.3 | 17.6 | 5.0 | 4.9 | 3.3 | 207 | 261 | 68.76 | 30.54 |
| LSD(.05) | 1.1 | 1.0 | 0.1 | 0.3 | 0.5 | 1 | 7 | 1.58 | 2.48 |
| CV | 3.2 | 5.9 | 2.8 | 5.1 | 13.8 | 1 | 3 | 2.30 | 8.13 |

*Visual ratings, lowest number = least preferred expression, highest number = most preferred expression, for trait.

EXAMPLE 14
Performance of Maize Hybrid RPG824 in German Official Silage Trials

Table 22 summarizes the results of the 1998 German official silage trials. Maize hybrid RPG824 flowered later than any other check hybrid and had a higher plant height. The cold susceptibility rating for maize hybrid RPG824 was equal to those for Prinz, lower than those of Symphony, and greater than those of the other check hybrids. The percentage lodging at harvest for RPG824 was less than that for Fernando, equal to that of Galice, and greater than those of other check hybrids. The Fusarium rating for maize hybrid RPG824 was less than those for Symphony, Probat, and Lenz, equal to that for Fernando, and greater than those for the other check hybrids. The rating for smutted plants for maize hybrid RPG824 was equal to or greater than those for Fernando, Symphony, Probat, Attribut, Santiago, and Harpun and was less than those for the other check hybrids. The Ostrinia ratings of maize hybrid RPG824 was higher than that of any check. European Corn Borer ratings of maize hybrid RPGS24 were less than those for Fernando, Probat, Prinz, Santiago, and Turkus and were equal to or greater than those of the other checks. The stover yield estimate for maize hybrid RPG824 was similar to that for Fernando, less than that for Galice, and greater than those of the other check hybrids. The dry matter yield of maize hybrid RPG824 was higher than those of the check hybrids and the dry matter percentage estimate for maize hybrid RPG824 was equal to the average of the checks.

TABLE 22

1998 GERMAN OFFICIAL SILAGE TRIALS*

|  | Emergence Date | Flowering Date | Plant Height (cm) | Cold Susceptibility (Rating) | Harvest Lodging (%) | Tillers/ Plant | Fusarium (Rating) | SMUT (Ratings) |
|---|---|---|---|---|---|---|---|---|
| No. Locations | 15 | 14 | 13 | 3 | 8 | 11 | 3 | 5 |
| HARPUN | 10.05.98 | 14.07.98 | 257 | 2.2 | 1 | 1.2 | 1.0 | 3 |
| TÜRKIS | 10.05.98 | 14.07.98 | 257 | 1.8 | 2 | 1.4 | 1.0 | 5 |
| LENZ | 10.05.98 | 13.07.98 | 244 | 2.0 | 1 | 1.2 | 1.6 | 5 |
| Check Avg. | 10.05.98 | 14.07.98 | 253 | 2.0 | 1 | 1.3 | 1.2 | 4 |
| SANTIAGO | 10.05.98 | 14.07.98 | 233 | 1.8 | 0 | 1.3 | 1.0 | 2 |
| PRINZ | 10.05.98 | 13.07.98 | 249 | 2.3 | 0 | 1.2 | 1.6 | 4 |
| ATTRIBUT | 10.05.98 | 16.07.98 | 261 | 1.7 | 0 | 1.0 | 1.0 | 2 |
| PROBAT | 10.05.98 | 14.07.98 | 255 | 1.9 | 1 | 1.1 | 1.7 | 0 |
| SYMPHONY | 10.05.98 | 12.07.98 | 244 | 2.5 | 1 | 2.7 | 1.5 | 2 |
| GALICE | 10.05.98 | 16.07.98 | 276 | 1.6 | 4 | 2.4 | 1.0 | 9 |
| FERNANDO | 10.05.98 | 16.07.98 | 269 | 2.0 | 7 | 2.0 | 1.3 | 3 |
| RPG824 | 10.05.98 | 19.07.98 | 277 | 2.3 | 4 | 1.4 | 1.3 | 3 |

|  | Ostrinia (Rating) | European Corn Borer (Rating) | Stover (dt/ha) | Dry Matter (dt/ha) | Dry Matter (%) | Starch (%) | Starch/ Check (%) |
|---|---|---|---|---|---|---|---|
| No. Locations | 1 | 5 | 12 | 12 | 12 | 12 | 12 |
| HARPUN | 1.0 | 2 | 622 | 198.6 | 32.2 | 30.0 | 97 |
| TÜRKIS | 1.0 | 4 | 596 | 197.6 | 33.6 | 31.4 | 101 |
| LENZ | 1.5 | 2 | 598 | 197.8 | 33.5 | 31.6 | 102 |
| Check Avg. | 1.2 | 3 | 605 | 198.0 | 33.1 | 31.0 | 31 |

TABLE 22-continued

1998 GERMAN OFFICIAL SILAGE TRIALS*

| SANTIAGO | 1.5 | 4 | 607 | 197.6 | 33.2 | 33.2 | 107 |
|---|---|---|---|---|---|---|---|
| PRINZ | 1.0 | 4 | 598 | 198.8 | 33.6 | 33.2 | 107 |
| ATTRIBUT | 2.0 | 2 | 639 | 213.1 | 33.9 | 29.3 | 95 |
| PROBAT | 1.5 | 4 | 582 | 196.5 | 34.3 | 34.3 | 111 |
| SYMPHONY | 1.0 | 3 | 564 | 192.1 | 34.4 | 34.7 | 112 |
| GALICE | 1.5 | 3 | 697 | 209.9 | 30.6 | 29.2 | 94 |
| FERNANDO | 1.0 | 4 | 666 | 214.4 | 32.4 | 31.3 | 101 |
| RPG824 | 2.5 | 3 | 668 | 218.6 | 33.1 | 31.7 | 102 |

*Visual ratings, lowest number = least desired expression, highest number = most desired expression, for trait;
Fusarium, rating for Fusarium stalk rot (*Fusarium moniliforme*);
Smut, rating for infection by common smut (*Ustilago maydis*);
Ostrinia, rating for Asian Corn Borer (*Ostrinia furnacalis*); and
European corn borer, rating for European Corn Borer (*Ostrinia nubilalis*).

EXAMPLE 15
Performance of Maize Hybrid RPG824 in Swiss Official Silage Trials Table 23 summarizes the performance of maize hybrid RPG824 in the 1998 Swiss official silage trials over sixteen locations. Maize hybrid RPG824 had a significantly higher early vigor score than Silpro and Accent and a significantly higher plant height than any check hybrid. The ear height of maize hybrid RPG824 was significantly higher than those of the checks, except in the case of Silpro. The visual rating for lodging for maize hybrid RPG824 was not significantly different than that for Silpro, was significantly lower than that for Goldmeru, and was significantly higher than those of the other check hybrids. The digestibility estimate for maize hybrid RPG824 was significantly lower than that for Attribut, Accent, and Goldmeru and not significantly different than the other check hybrids. The starch estimate for maize hybrid RPG824 was significantly higher than those for LG 2265 and Accent, was significantly lower than that for Goldmeru, and not significantly different than those of the other checks. The percentage grain expressed on a dry matter basis estimate for maize hybrid RPG824 was significantly lower than those for Silpro, LG 2265, and Goldmeru and significantly higher than that for Attribut. The cellulose estimate for maize hybrid RPG824 was significantly higher than that for Goldmeru. The NDF estimate for maize hybrid RPG824 was significantly higher than those for Attribut and Goldmeru. The total nitrogen matter estimate for maize hybrid RPG824 was significantly higher than that for Attribut and significantly lower than those for Silpro and Goldmeru. The total stover yield and total dry matter yield estimates for maize hybrid RPG824 were significantly higher than those for the check hybrids. The percent dry matter estimate for maize hybrid RPG824 was significantly lower than those for Goldmeru, Accent, Attribut, and LG 2265. The ear height/plant height ratio for maize hybrid RPG824 was significantly higher than those for Goldmeru and Attribut. Maize hybrid RPG824 silked one day later than Attribut and Accent and two days later than Goldmeru. The energy for milk and energy for meat estimates for maize hybrid RPG824 were significantly lower than those of the check hybrids, except for those of Silpro.

TABLE 23

1998 SWISS OFFICIAL SILAGE TRIALS
(16 LOCATIONS)

| | EARLY VIGOR (1–5) | PLANT HEIGHT (cm) | EAR HEIGHT (cm) | LODGING (Visual Score) | DIGESTIBILITY | STARCH (g/kg) | % GRAIN (Dry Matter Basis) |
|---|---|---|---|---|---|---|---|
| GOLDMERU | 2.1 | 243 | 102 | 4.0 | 753.8 | 278 | 49 |
| ACCENT | 3.4 | 240 | 107 | 1.7 | 752.0 | 353 | 46 |
| ATTRIBUT | 2.4 | 263 | 110 | 1.6 | 755.3 | 362 | 43 |
| LG22.65 | 2.4 | 258 | 110 | 1.4 | 750.2 | 351 | 47 |
| SILPRO | 3.0 | 276 | 127 | 3.0 | 743.7 | 368 | 49 |
| RPG824 | 3.5 | 293 | 132 | 3.4 | 744.0 | 364 | 46 |
| CV % | 25.2 | 2 | 4 | 36.7 | 1.3 | 3 | 4 |
| LSD (.05) | 0.5 | 11 | 7 | 1.0 | 7.1 | 9 | 1 |
| LSD (.01) | 0.6 | 14 | 10 | 1.3 | 9.4 | 12 | 2 |

| | CELLULOSE (g/kg) | NDF (g/kg) | TOTAL NITROGEN (g/kg) | TOTAL STOVER (dt/ha) | TOTAL DRY MATTER (dt/ha) | % DRY MATTER | ROOT LODGING (%) | HARVEST LODGING (%) | BROKEN PLANTS (%) |
|---|---|---|---|---|---|---|---|---|---|
| GOLDMERU | 161 | 383 | 67 | 574.2 | 201.1 | 35.2 | 0.0 | 0.3 | 0.8 |
| ACCENT | 187 | 398 | 65 | 621.6 | 213.9 | 34.6 | 5.0 | −0.0 | 1.3 |
| ATTRIBUT | 182 | 389 | 62 | 661.0 | 229.4 | 34.9 | 6.8 | 0.1 | 1.1 |
| LG22.65 | 184 | 396 | 63 | 647.8 | 224.9 | 34.9 | 5.0 | 0.0 | 1.7 |
| SILPRO | 182 | 394 | 70 | 639.2 | 212.3 | 33.3 | 3.5 | −0.9 | 1.1 |
| RPG824 | 185 | 396 | 64 | 722.4 | 239.6 | 33.4 | 4.5 | 2.8 | 2.1 |
| CV % | 3 | 3 | 4 | 4.3 | 4.0 | 2.4 | 97.5 | 206.0 | 194.9 |
| LSD (.05) | 4 | 6 | 2 | 18.6 | 6.0 | 0.6 | | 0.5 | |
| LSD (.01) | 5 | 10 | 2 | 24.6 | 8.0 | 0.8 | | 0.7 | |

TABLE 23-continued

1998 SWISS OFFICIAL SILAGE TRIALS
(16 LOCATIONS)

|  | PLANTS/M$^2$ | EAR HEIGHT/ PLANT HEIGHT (%) | FLOWERING FEMALE (Days From Planting) | ENERGY FOR MILK (mJ/kg) | ENERGY FOR MEAT (mJ/kg) |
|---|---|---|---|---|---|
| GOLDMERU | 9.9 | 42 | 72 | 7.0 | 7.3 |
| ACCENT | 10.6 | 44 | 73 | 6.9 | 7.3 |
| ATTRIBUT | 10.5 | 42 | 73 | 7.0 | 7.3 |
| LG22.65 | 10.6 | 43 | 74 | 6.9 | 7.3 |
| SILPRO | 9.9 | 47 | 74 | 6.8 | 7.2 |
| RPG824 | 10.4 | 45 | 74 | 6.8 | 7.2 |
| CV% | 4.5 | 3 | 1 | 1.7 | 2.1 |
| LSD (.05) | 0.3 | 3 | 1 | 0.1 | 0.1 |
| LSD (.01) | 0.4 | 3 | 2 | 0.1 | 0.1 |

EXAMPLE 16
Performance of Maize Hybrid RPG824 in Belgian Official Silage Trials Table 24 summarizes the results of the 1998 Belgian official silage trials. The stover yield of maize hybrid RPG824 was higher than those of the checks and with the exception of Anjou 258, the earliness rating was lower. The early vigor score of maize hybrid RPG824 was higher than those for LG 2243, Mercator, and Banguy, and was lower than those of the other checks. Maize hybrid RPG824 had the lowest percentage smutted plants, the highest plant height and the highest ear height. With the exception of Anjou 258, maize hybrid RPG824 was later in flowering than the other checks. Again with the exception of Anjou 258, maize hybrid RPG824 had the lowest dry matter percentage.

To summarize, maize hybrid RPG824 produces consistently high grain and stover yields over a wide series of environments, dries down exceptionally well, and has average to excellent standability.

the developing grain is at the half-milk stage. When the grain is physiologically mature, it is harvested, usually with combines, then dried to a moisture content sufficiently low for storage. The grain may then be used for feed, food, and industrial purposes, examples of which are disclosed herein.

Derivation

This invention is considered to include processes of developing derived maize inbred lines and plants, seeds, and parts resulting thereof. Processes of developing derived inbred lines include those processes, wherein single genes or alleles or some small plurality of genes or alleles are introgressed into RPG824, resulting in a derived hybrid which expresses the introgressed gene(s) or allele(s) (i.e. trait(s)), but otherwise retains the phenotype and genotype of RPG824 described herein. Examples of introgressed genes or alleles include genes from other maize plants, or alleles or genes originating from other species. Non-limiting examples of these genes or alleles are disclosed in Coe et al., "The Genetics of Corn," IN Corn and Corn Improvement, G. F. Sprague and J. W. Dudley, Editors, American Society of

TABLE 24

1998 BELGIAN OFFICIAL SILAGE TRIALS

| Variety | Stover Yield (kg/ha) | Yield (% Checks) | Earliness (Rating) | Lodging (Arcsin %) | Early Vigor (1–9) | SMUT (%) | Plant Height (cm) | Ear Height (cm) | Flowering (Days) (Deviations From Checks) | Stalk Fusarium (%) | Harvest Lodging (%) | Dry Matter (%) | Yield/ Checks |
|---|---|---|---|---|---|---|---|---|---|---|---|---|---|
| Anjou 258 | 22438.7 | 105.1 | 31.9 | 1.8 | 7.2 | 0.8 | 272 | 104 | 3.7 | 0.0 | 0.3 | 92.2 | 109.2 |
| Banguy | 20912.4 | 98.0 | 34.6 | 0.0 | 6.4 | 0.5 | 247 | 91 | 0.0 | 0.0 | 0.0 | 99.9 | 101.8 |
| Dirk | 21439.2 | 100.5 | 34.0 | 1.8 | 7.2 | 0.9 | 259 | 114 | −0.7 | 0.0 | 0.3 | 98.3 | 104.4 |
| Mercator | 21424.0 | 100.4 | 34.2 | 1.8 | 6.7 | 0.8 | 256 | 111 | 1.0 | 0.0 | 0.3 | 98.9 | 104.3 |
| LG22.43 | 20500.8 | 96.1 | 33.8 | 0.0 | 6.6 | 1.4 | 260 | 102 | 2.7 | 0.2 | 0.0 | 97.6 | 99.8 |
| RPG824 | 23031.9 | 107.9 | 32.9 | 0.0 | 6.9 | 0.3 | 281 | 120 | 3.3 | 0.0 | 0.0 | 95.0 | 112.1 |

Further Embodiments of the Invention

Grain and Silage Production

This invention is contemplated to include producing stover and grain when maize hybrid RPG824 is grown. Typically seed of this hybrid is planted in soil with adequate moisture to support germination, emergence, and subsequent growth and development. Alternatively, soil moisture is added by irrigation. Normal cultural practices to achieve proper soil fertility and manage weeds, insects, and diseases may be undertaken during the growing season as necessary. These cultural practices are known to persons of skill in the art and vary widely according to particular geographic regions, grower preferences, and economic considerations. The corn plants may be chopped for silage, typically when Agronomy, Madison, Wis. (1988), the disclosure of which is hereby incorporated by reference. Other nonlimiting examples of genes or alleles which might be introgressed into the present invention are disclosed hereinbelow. Methods of introgression may include such protocols as tissue culture to induce somoclonal variation, impaling plant cells with needle-like bodies, and transformation.

Exemplary transformation protocols are disclosed, e.g., by U.S. Pat. No. 5,302,523 to Coffee et al. (transformed maize via needle-like bodies); U.S. Pat. No. 5,384,253 to Krzyzek et al. (electroporation); U.S. Pat. No. 5,371,003 to Murray et al. (transformation via tissues within horizontal electrophoresis gel in the presence of non-pulsed electric current); U.S. Pat. No. 5,591,616 to Hiei et al.

(Agrobacterium-mediated transformation); U.S. Pat. No. 5,569,597 to Grimsley et al. (Agrobacterium-mediated maize transformation); U.S. Pat. 5,877,023 to Sautter et al. (microprojectile-facilitated transformation); U.S. Pat. No. 5,736,369 to Bowen et al. (microprojectile-facilitated transformation); U.S. Pat. Nos. 5,886, and 5,990,387 to Tomes et al. (microprojectile-facilitated transformation); U.S. Pat. No. 5,776,900 to Shillito et al. (regeneration of maize protoplasts transformed with electroporation and polyethylene glycol (PEG)); U.S. Pat. Nos. 5,767,367 and 5,792,936 to Dudits et al. (regeneration of PEG-transformed protoplasts of auxin-autrotrophic maize genotype); U.S. Pat. 5,780,708 and 5,990,390 to Lundquist et al. (fertile, microprojectile-facilitated transgenic maize plants expressing dalapon resistance); U.S. Pat. Nos. 5,780,709 and 5,919,675 to Adams et al. (microprojectile- and electroporation-facilitated maize transformants); U.S. Pat. No. 5,932,782 to Bidney (microprojectile-delivered Agrobacterium); U.S. Pat. No. 5,981,840 to Zhao et al. (Agrobacterium-transformed maize); and U.S. Pat. No. 5,994,624 to Trolinder et al. (maize transformation via recombinant Agrobacterium DNA injected into plant tissues via needleless injection device), the contents of each hereby incorporated by reference.

Further Uses

There are many analytical methods available to determine the heterozygotic and phenotypic stability of maize hybrids. The oldest and most traditional method of analysis is observation of their phenotypic traits. Data scoring these traits are usually collected in field experiments over the life of the maize plants to be examined. Phenotypic characteristics often observed are for traits associated with plant, ear, and kernel morphology, insect and disease reaction (resistance or tolerance), maturity, and grain and stover yield.

In addition to phenotypic observations, the genotype of a plant can also be determined. Many laboratory-based techniques are available to determine, compare and characterize plant genotypes. Among these techniques are isozyme electrophoresis, restriction fragment length polymorphisms (RFLPs), randomly amplified polymorphic DNAs (RAPDs), arbitrarily primed polymerase chain reaction (AP-PCR), DNA amplification fingerprinting (DAF), sequence characterized amplified regions (SCARs), amplified fragment length polymorphisms (AFLPs), and simple sequence repeats (SSRs) (microsatellites).

The most widely used of these laboratory techniques are isozyme electrophoresis and RFLPs , e.g., M. Lee, "Inbred Lines of Maize and Their Molecular Markers," The Maize Handbook, (Springer-Verlag, New York, Inc. 1994, at 423–432), the disclosure of which is hereby incorporated by reference. Isozyme electrophoresis is a useful tool in determining genetic composition, although a relatively low number of available markers, as well as a low number of alleles, are present among maize inbreds. By contrast, RFLPs have the advantage of revealing an exceptionally high degree of allelic variation in maize, as well as an almost limitless number of available markers.

As used herein, the term "plant" includes whole or entire plants and parts thereof. Such exemplary plant parts may include plant cells, plant protoplasts, plant cell tissue cultures, plant calli, plant clumps, plant cell suspension cultures, and plant protoplasts. Also included within the definition of the term "plant" are plant cells present in plants or parts of plants, e.g., zygotes, embryos, embryonic organs, pollen, ovules, flowers, seeds, ears, cobs, leaves, husks, stalks, roots, root tips, anthers, and silks.

Tissue Culture of Maize

Regeneration of maize plants by tissue culture methods is now an exercise requiring only routine experimentation to a person skilled in the art. For example, Duncan et al. (Planta 165:322–332 (1985)) reported 97% of the plant genotypes cultured produced calli capable of plant regeneration. Plants were regenerated from 91% of the calli from another set of inbreds and hybrids in a subsequent experiment.

Songstad et al., (Plant Cell Reports, 7:262–265 (1988)) reported several media additions enhancing regenerability of callus of two inbred lines. Other published reports also indicated "nontraditional" tissues capable of producing somatic embryogenesis and plant regeneration. For example, Rao, et al. (Maize Genetics Cooperation Newsletter, 60:64–65 (1986)) reported somatic embryogenesis from glume callus cultures. Conger, et al. (Plant Cell Reports, 6:345–347 (1987)) reported somatic embryogenesis from tissue cultures of maize leaf segments. Thus, it is clear that the state of the art is such that these tissue culture methods of obtaining regenerated plants are routinely used with very high rates of success.

Maize tissue culture is described generally in European Patent Application, Publication 160,390, hereby incorporated by reference and with respect to inbred line B73 in U.S. Pat. No. 5134,074 to Gordon et al. Maize tissue culture procedures are also described by Green et al., "Plant Regeneration in Tissue Culture of Maize," Maize for Biological Research (Plant Molecular Biology Association, Charlottesville, Va. 1982, at 367–372) and by Duncan, et al., "The Production of Callus Capable of Plant Regeneration from Immature Embryos of Numerous *Zea Mays* Genotypes,"  165 Planta 322–332 (1985), each hereby incorporated by reference. Thus, another aspect of this invention is to provide cells which undergo growth and differentiation and subsequently produce maize plants with the physiological and morphological characteristics of maize hybrid RPG824.

Somaclonal variation within inbred lines which have undergone tissue culture and regeneration have been reported by Edallo et al. ("Chromosome Variation and Frequency of Spontaneous Mutants Associated With In Vitro Culture and Plant Regeneration in Maize," Maydica 26: 39–56 (1981)); McCoy et al. ("Chromosome Stability in Maize (*Zea Mays* L.) Tissue Culture and Sectoring in Some Regenerated Plants," Can. J. Genet. Cytol. 24: 559–565 (1982)), Earle et al. ("Somaclonal Variation in Progeny of Plants From Corn Tissue Culture," pp. 139–152, In R. R. Henke et al. (ED.) Tissue Culture in Forestry and Agriculture, Plenum Press, N.Y. (1985)); and Lee et al. ("Agronomic Evaluation of Inbred Lines Derived From Tissue Cultures of Maize," Theor. Appl. Genet. 75: 841–849 (1988)), the disclosures of which are incorporated by reference. Hence, genetic variation and derived lines may be developed from this invention by tissue culture protocols.

The utility of maize hybrid RPG824 also extends to crosses with other species. Suitable species will be of the family Gramineae, and especially genera such as Zea, Tripsacum, Coix, Schlerachne, Polytoca, Chionachne, and Trilobachne, of the tribe Maydeae. Potentially suitable for crosses with maize hybrid RPG824 may be the various varieties of grain sorghum, Sorghum bicolor (L.) Moench.

Transformation of Maize

Molecular biological techniques now allow genes encoding specific protein products to be isolated and characterized. It has long been viewed as advantageous to modify maize plant genomes to contain and express foreign genes, or additional, or modified versions of native or endogenous genes (perhaps driven by different promoters) to alter traits of a plant in a specific, directed manner. Such foreign, additional and/or modified genes are referred to herein collectively as "transgenes" and several methods for producing transgenic plants have been developed. Accordingly, embodiments of this invention also include derived inbreds which are developed from transformed versions of maize hybrid RPG824.

Plant transformation requires construction of an expression vector to function in plant cells. Such an expression vector includes DNA. The vector DNA, in turn, includes a gene under control of, or operatively linked to, a regulatory element such as a promoter. The expression vector may contain one or more such operably linked gene/regulatory element combinations; may be in the form of a plasmid; and can also be used alone, or in combination with other plasmids, to transform maize plants using transformation methods such as those described below.

Marker Genes

Expression vectors usually include at least one genetic marker operably linked to a regulatory element such as a promoter. The regulatory element allows transformed cells containing the marker to be recovered either by negative or positive selection. Negative selection includes inhibiting growth of cells not containing the selectable marker gene. By contrast, positive selection includes screening for the product encoded by the genetic marker. Many commonly used selectable markers for identifying transformed plant cells are known in the art. Such exemplary selectable markers include genes encoding enzymes which metabolically detoxify a selective chemical agent such as an antibiotic or a herbicide. Other selectable markers include genes encoding an altered target which is insensitive to an inhibitor. A few positive selection methods are also known.

One commonly used selectable marker is the neomycin phosphotransferase II gene (nptII), isolated from transposon Tn5 and conferring resistance to kanamycin. Fraley et al., Proc. Natl. Acad. Sci. U.S.A., 80: 4803 (1983); U.S. Pat. No. 5,858,742 to Fraley et al. Another commonly used selectable marker gene is the hygromycin phosphotransferase gene conferring resistance to the antibiotic hygromycin. Vanden Elzen et al., Plant Mol. Biol., 5: 299 (1985).

Other selectable marker genes of bacterial origin conferring resistance to antibiotics include gentamycin acetyl transferase, streptomycin phosphotransferase, aminoglycoside-3'-adenyl transferase, and bleomycin resistance determinant. Hayford et al., Plant Physiol. 86: 1216 (1988); Jones et al., Mol. Gen. Genet., 210: 86 (1987); Svab et al., Plant Mol. Biol. 14: 197 (1990); and Hille et al., Plant Mol. Biol. 7: 171 (1986).

Still other selectable markers confer resistance to herbicides such as glyphosate, glufosinate, or bromoxynil. Comai et al., Nature 317: 741–744 (1985); Gordon-Kamm et al., Plant Cell 2: 603–618 (1990); and Stalker et al., Science 242: 419–423 (1988).

Yet other selectable marker genes include mouse dihydrofolate reductase, plant 5-enolpyruvylshikimate-3-phosphate synthase, and plant acetolactate synthase. Eichholtz et al., Somatic Cell Mol. Genet. 13: 67 (1987); Shah et al., Science 233: 478 (1986); and Charest et al., Plant Cell Rep. 8: 643 (1990).

Another class of marker genes useful in plant transformation requires screening putatively transformed plant cells rather than direct genetic selection of transformed cells. These genes are used to quantify or visualize spatial patterns of gene expression in specific tissues. Marker genes of this nature are frequently termed "reporter genes" because they can be fused to a gene or gene regulatory sequence to investigate gene expression. Commonly used genes for screening presumptively transformed cells include β-glucuronidase (GUS), β-galactosidase, luciferase and chloramphenicol acetyltransferase. Jefferson, Plant Mol. Biol. Rep. 5: 387 (1987); Teeri et al., EMBO J. 8: 343 (1989); Koncz et al., Proc. Natl. Acad. Sci. U.S.A. 84: 131 (1987); and De Block et al., EMBO J. 3: 1681 (1984). Until recently, methods for visualizing GUS activity required destruction of the living plant material. However, in vivo methods for visualizing GUS activity not requiring destruction of plant tissue are now available. Molecular Probes Publication 2908, Imagene Green™, p. 1–4 (1993); and Naleway et al., J. Cell Biol. 115: 151a (1991).

Another method of identifying rare transformation events includes using a gene encoding a dominant constitutive regulator of the *Zea mays* anthocyanin pigmentation pathway. Ludwig et al., Science 247: 449 (1990). A gene encoding for Green Fluorescent Protein (GFP) has been utilized as a marker for gene expression in prokaryotic and eukaryotic cells. Chalfie et al., Science 263: 802 (1994).

Promoters

Genes in expression vectors must be driven by a nucleotide sequence comprising a regulatory element such as a promoter. Several types of promoters are now known, as are other regulatory elements which can be used singly or in combination with promoters. As used herein "promoter" includes a region of DNA upstream from the initial site of transcription. The promoter is involved in recognizing and binding RNA polymerase and other proteins during transcription initiation. A "plant promoter" is a promoter capable of initiating transcription in plant cells.

Examples of promoters under developmental control include promoters which preferentially initiate transcription in certain tissues such as leaves, roots, seeds, fibers, xylem vessels, tracheids, or sclerenchyma. Such promoters are referred to as "tissue-preferred." Promoters initiating transcription only in certain tissues are referred to as "tissue-specific." A "cell type-specific" promoter primarily drives expression only in certain cell types present in specific organs, e.g., vascular cells in roots or leaves. An "inducible" promoter is a promoter under environmental control. Examples of environmental conditions affecting transcription by inducible promoters include anaerobic conditions or the presence of light. Tissue-specific, tissue-preferred, cell type-specific, and inducible promoters constitute the class of "non-constitutive" promoters. In contrast to non-constitutive promoters, "constitutive" promoters function under most environmental conditions.

A. Inducible Promoters

An inducible promoter may be operably linked to a gene to be expressed in maize. Optionally, the inducible promoter is operably linked to a nucleotide sequence encoding a signal sequence. The signal sequence, in turn, is operably linked to a gene to be expressed in maize. With an inducible promoter, the rate of transcription increases in response to an inducing agent.

Any inducible promoter can be used in conjunction with this invention. See, e.g., Ward et al. Plant Mol. Biol. 22: 361–366 (1993). Exemplary inducible promoters include, but are not limited to, the promoter the ACEI system responding to copper (Mett et al. PNAS 90: 4567–4571 (1993)); the maize In2 gene responding to benzenesulfonamide herbicide safeners (Hershey et al., Mol. Gen. Genetics 227: 229–237 (1991) and Gatz et al., Mol. Gen. Genetics 243: 32–38 (1994)); or the Tet repressor from Tn10 (Gatz et al., Mol. Gen. Genet. 227: 229–237 (1991)). One suitable inducible promoter responds to an inducing agent to which plants do not normally respond. One such exemplary inducible promoter is induced by a glucocorticosteroid hormone. Schena et al., Proc. Natl. Acad. Sci. U.S.A. 88: 0421 (1991).

B. Constitutive Promoters

A constitutive promoter is operably linked to a gene to be expressed in maize. Alternatively, the constitutive promoter is operably linked to a nucleotide sequence encoding a signal sequence which, in turn, is operably linked to a gene to be expressed in maize. Many different constitutive promoters can be utilized with respect to the hybrid of this invention. Exemplary constitutive promoters include, but are not limited to, promoters from plant viruses such as the 35S promoter from CaMV (Odell et al., Nature 313: 810–812 (1985); U.S. Pat. No. 5,858,742 to Fraley et al.); promoters from such plant genes as rice actin (McElroy et al., Plant Cell 2: 163–171 (1990)); ubiquitin (Christensen et al., Plant Mol. Biol 12: 619–632 (1989) and Christensen et al., Plant Mol. Biol. 18: 675–689 (1992)); pEMU (Last et al., Theor. Appl. Genet. 81: 581–588 (1991)); MAS (Velten et al., EMBO J. 3: 2723–2730 (1984)) and maize H3 histone (Lepetit et al., Mol. Gen. Genet. 231: 276–285 (1992) and Atanassova et al., Plant Journal 2(3): 291–300 (1992)); and he ALS promoter, a XbaI/NcoI fragment 5' to the Brassica napus ALS3 structural gene or a nucleotide sequence with substantial sequence similarity (PCT Application No. WO 96/30530).

C. Tissue-specific or Tissue-Preferred Promoters

A tissue-specific promoter is operably linked to a gene to be expressed in maize. Optionally, the tissue-specific promoter is operably linked to a nucleotide sequence encoding a signal sequence which is operably linked to a gene to be expressed in maize. Plants transformed with a gene operably linked to a tissue-specific promoter produce the protein product of the transgene exclusively, or preferentially, in a specific tissue.

Any tissue-specific or tissue-preferred promoter can be introgressed into the hybrid of this invention. Exemplary tissue-specific or tissue-preferred promoters include, but are not limited to, a root-preferred promoter, such as that from the phaseolin gene (Murai et al., Science 23: 476–482 (1983) and Sengupta-Gopalan et al., Proc. Natl. Acad. Sci. USA 82: 3320–3324 (1985)); a leaf-specific and light-induced promoter such as that from cab or rubisco (Simpson et al., EMBO J. 4(11): 2723–2729 (1985) and Timko et al., Nature 318: 579-582 (1985)); an another-specific promoter such as that from LAT52 (Twell et al., Mol. Gen. Genet. 217: 240–245 (1989)); a pollen-specific promoter such as that from Zm13 (Guerrero et al., Mol. Gen. Genet. 224: 161–168 (1993)); and a microspore-preferred promoter such as that from apg (Twell et al., Sex. Plant Reprod. 6: 217–224 (1993)).

Signal Sequences for Targeting Proteins to Subcellular Compartments

Proteins produced by transgenes may be transported to a subcellular location such as a chloroplast, vacuole, peroxisome, glyoxysome, cell wall or mitochondrion, or for secretion into the apoplast, by operably linking the nucleotide sequence encoding a signal sequence to the 5' and/or 3' region of a gene encoding the protein of interest. Targeting sequences at the 5' and/or 3' end of the structural gene may determine where the encoded protein is ultimately compartmentalized during protein synthesis and processing. The presence of a signal sequence directs a polypeptide to an intracellular organelle, a subcellular compartment, or to the apoplast for secretion. Many signal sequences are known in the art. See, e.g., Becker et al., Plant Mol. Biol. 20: 49 (1992); P. S. Close, Master's Thesis, Iowa State University (1993); Knox, et al., "Structure and Organization of Two Divergent Alpha-Amylase Genes From Barley," Plant Mol. Biol. 9: 3–17 (1987); Lerner et al., Plant Physiol. 91: 124–129 (1989); Fontes et al., Plant Cell 3: 483–496 (1991); Matsuoka et al., Proc. Natl. Acad. Sci. 88: 834 (1991); Gould et al., J. Cell Biol 108: 1657 (1989); Creissen et al., Plant J. 2: 129 (1991); Kalderon et al., "A short amino acid sequence able to specify nuclear location", Cell 39: 499–509 (1984); and Stiefel et al., "Expression of a maize cell wall hydroxyproline-rich glycoprotein gene in early leaf and root vascular differentiation," Plant Cell 2: 785–793 (1990).

Foreign Protein Genes and Agronomic Genes

A foreign protein can be produced by transgenic plants of this invention and may further be produced in commercial quantities. Thus, techniques for selection and propagation of transformed plants understood in the art provide a plurality of transgenic plants which may be harvested in a conventional manner. A foreign protein expressed in the transgenic plants can then be extracted either from a specific tissue or from total harvested plant biomass. Protein extraction from plant biomass can be accomplished by methods which are discussed, e.g., by Heney et al., Anal. Biochem. 114: 92–96 (1981).

Thus, this invention is contemplated to include transformed, therefore derived, embodiments of maize hybrid RPG824 and inbred lines derived therefrom. In another embodiment, the biomass of interest is the vegetative tissue of maize hybrid RPG824. In yet another embodiment, the biomass of interest is grain (seed). For transgenic plants, a genetic map can be generated, primarily via conventional Restriction Fragment Length Polymorphisms (RFLP), Polymerase Chain Reaction (PCR) analysis, and Simple Sequence Repeats (SSR), which identify the approximate chromosomal location of the integrated DNA. For exemplary methodologies in this regard see Glick et al., Methods in Plant Molecular Biology and Biotechnology, 269–284 (CRC Press, Boca Raton, 1993). Map information concerning chromosomal location is useful for proprietary protection of a given transgenic plant. Hence, if unauthorized propagation occurs and crosses of the present hybrid are made to other germplasm, the map of the integration region can be compared to similar maps of suspect plants, thereby determining whether the suspect plants have a common parentage with the subject plant. Map comparisons require hybridization and subsequent RFLP, PCR, SSR and/or sequencing, all known techniques.

Agronomic genes can be expressed in the transformed plants of this invention. More particularly, plants of this invention can be transformed, or otherwise derived, to express various phenotypes of agronomic interest. Exemplary genes implicated in this regard include, but are not limited to, those categorized below.

1. Genes Conferring Resistance To Pests or Diseases (A) Plant disease resistance genes. Plant defenses are often activated by specific interaction between the product of a disease resistance gene (R) in the plant and the product of a corresponding avirulence (Avr) gene in the pathogen. A plant variety can be transformed with a cloned disease resistance gene to develop plants resistant to pathogen strains. See, e.g., Jones et al., Science 266: 789 (1994) (cloning of tomato Cf-9 gene resistant to *Cladosporium fulvum*); Martin et al., Science 262: 1432 (1993) (tomato Pto gene resistant to *Pseudomonas syringae* pv. tomato encoding a protein kinase); Mindrinos et al., Cell 78:1089 (1994) (Arabidopsis RSP2 gene resistant to *Pseudomonas*

*syringae*); U.S. Pat. No. 5,789,214 to Ryals et al. (chemically regulatable DNA sequences regulating transcription of pathogenesis-related proteins); and PCT Patent Application Publication WO95/16776 to Putman et al. (derivatives of tachyplesin peptide with antimicrobial activity against plant pathogens).

(B) *Bacillus thuringiensis* (B.t.) proteins, derivatives thereof, or a synthetic polypeptides modeled thereon. See, e.g., Geiser et al., Gene 48: 109 (1986) (cloning and nucleotide sequencing of Bt δ-endotoxin gene). DNA molecules encoding δ-endotoxin genes are designated as ATCC Accession Nos. 40098, 67136, 31995 and 31998 and can be purchased from American Type Culture Collection, Manassas, Va. 20110.

(C) Lectins. See, e.g., Van Damme et al., Plant Molec. Biol. 24: 25 (1994) (nucleotide sequences of *Clivia miniata* mannose-binding lectin genes).

(D) Vitamin-binding proteins such as avidin. See e.g., PCT Application No. US93/06487 (avidin and avidin homologues as larvicides against insect pests).

(E) Enzyme inhibitors such as protease inhibitors or amylase inhibitors. See, e.g., Abe et al., J. Biol. Chem. 262: 16793 (1987) (nucleotide sequence of rice cysteine proteinase inhibitor); Huub et al., Plant Molec. Biol. 21: 985 (1993) (nucleotide sequence of cDNA encoding tobacco proteinase inhibitor I); and Sumitani et al., Biosci. Biotech. Biochem. 57: 1243 (1993) (nucleotide sequence of *Streptomyces nitrosporeus* α-amylase inhibitor).

(F) An insect-specific hormone or pheromone such as an ecdysteroid and juvenile hormone, a variant thereof, a mimetic based thereon, or an antagonist or agonist thereof. See, e.g., Hammock et al., Nature 344: 458 (1990), (baculovirus expression of cloned juvenile hormone esterase, an inactivator of juvenile hormone).

(G) Insect-specific peptides or neuropeptides disrupting pest physiologies. See, e.g., Regan, Biol. Chem. 269: 9 (1994) (expression cloning yields DNA coding for insect diuretic hormone receptor); and Pratt et al., Biochem. Biophys. Res. Comm. 163: 1243 (1989) (allostatin identified in *Diploptera puntata*); U.S. Pat. No. 5,266,317 to Tomalski et al. (genes encoding insect-specific, paralytic neurotoxins).

(H) Insect-specific venoms produced in nature by, e.g., snakes, wasps. See, e.g., Pang et al., Gene 116: 165 (1992) (heterologous expression in plants of a gene coding a scorpion insectotoxic peptide).

(I) Enzymes responsible for hyperaccumulation of monterpenes, a sesquiterpenes, steroids, hydroxamic acids, phenylpropanoid derivatives or other non-protein molecules with insecticidal activity.

(J) Enzymes involved in the modification, including post-translational modification, of biologically active molecules. Such enzymes are contemplated to include natural or synthetic glycolytic enzymes, proteolytic enzymes, lipolytic enzymes, nucleases, cyclases, transaminases, esterases, hydrolases, phosphatases, kinases, phosphorylases, polymerases, elastases, chitinases and glucanases. See, e.g., PCT Application No. WO 93/02197 to Scott et al. (callase gene nucleotide sequence). DNA molecules containing chitinase-encoding sequences can be obtained, e.g., from the ATCC under Accession Nos. 39637 and 67152. See, also Kramer et al., Insect Biochem. Molec. Biol. 23: 691 (1993) (nucleotide sequence of cDNA-encoding tobacco hookworm chitinase); and Kawalleck et al., Plant Molec. Biol. 21: 673 (1993) (nucleotide sequence of the parsley ubi4-2 polyubiquitin gene).

(K) Molecules stimulating signal transduction. See, e.g., Botella et al., Plant Molec. Biol. 24: 757 (1994) (nucleotide sequences for mung bean calmodulin cDNA clones); and Griess et al., Plant Physiol. 104: 1467 (1994) (nucleotide sequence of maize calmodulin cDNA clone).

(L) Hydrophobic moment peptides. See, e.g., PCT Application No. WO95/16776 (peptide derivatives of Tachyplesin-inhibiting fungal plant pathogens) and PCT Application No. WO95/18855 (synthetic antimicrobial peptides conferring disease resistance).

(M) Membrane permeases, channel formers, or channel blockers. See, e.g., Jaynes et al., Plant Sci. 89: 43 (1993) (heterologous expression of cecropin-β lytic peptide analog rendering transgenic tobacco plants resistant to Pseudomonas solanacearum).

(N) Viral-invasive proteins or complex toxins derived therefrom. For example, the accumulation of viral coat proteins in transformed plant cells imparting resistance to viral infection and/or disease development effected by the virus from which the coat protein gene is derived, as well as to related viruses. See, e.g., Beachy et al., Ann. Rev. Phytopathol. 28: 451 (1990). Coat protein-mediated resistance has been conferred on transformed plants against alfalfa mosaic virus, cucumber mosaic virus, tobacco streak virus, potato virus X, potato virus-Y, tobacco etch virus, tobacco rattle virus and tobacco mosaic virus. Id.

(O) Insect-specific antibodies or immunotoxins derived therefrom. An antibody targeted to a critical metabolic function in the insect gut inactivating an affected enzyme, thereby killing the insect. Cf. Taylor et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via single-chain antibody fragment production).

(P) Virus-specific antibodies. See, e.g., Tavladoraki et al., Nature 366: 469 (1993), (transgenic plants expressing recombinant antibody genes are protected from virus attack), hereby incorporated by reference.

(Q) Developmental-arrestive proteins produced by pathogens or parasites. See, e.g., Lamb et al., Bio/Technology 10: 1436 (1992) (fungal endo α-1,4-D-polygalacturonases facilitating fungal colonization and plant nutrient release by solubilizing plant cell wall homo-α-1,4-D-galacturonase); and Toubart et al., Plant J. 2: 367 (1992) (cloning and characterization of a gene encoding bean endopolygalacturonase-inhibiting protein).

(R) Developmental-arrestive proteins produced by plants. See, e.g., Logemann et al., Bio/Technology 10: 305 (1992) (increased resistance to fungal disease in transgenic plants expressing barley ribosome-inactivating gene).

2. Genes Conferring Resistance To Herbicides (A) Herbicides inhibiting growing points or meristems such as imidazolinone or a sulfonylurea. Exemplary genes in this category encode mutant ALS and AHAS enzymes, respectively described by Lee et al., EMBO J. 7: 1241 (1988); and Miki et al., Theor. Appl. Genet. 80: 449 (1990).

(B) Glyphosate resistance (imparted by mutant 5-enolpyruvl-3-phosphoshikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cyclohexones (ACCase inhibitor-encoding genes). See, e.g., U.S. Pat. No. 4,940,835 to Shah et al., (EPSP clone conferring glyphosate resistance). A DNA molecule encoding a mutant aroA gene can be obtained under ATCC Accession No. 39256. The nucleotide sequence of such a mutant gene is disclosed in U.S. Pat. No. 4,769,061 to Comai. European Patent Application No. 0 333 033 to Kumada et al. and U.S. Pat. No. 4,975,374 to Goodman et al. disclose nucleotide sequences of glutamine synthetase genes conferring resistance to herbicides such as L-phosphinothricin. A nucleotide sequence of a phosphinothricin-acetyl-transferase gene is disclosed in European Patent Application 0 242 246 to Leemans et al. De Greef et al., Bio/Technology 7: 61 (1989), describe the production of transgenic plants expressing chimeric bar genes coding for phosphinothricin acetyl transferase activity. Exemplary genes conferring resistance to phenoxy proprionic acids and cyclohexones, such as sethoxydim and haloxyfop, are the Acc1-S1, Acc1-S2 and Acc1-S3 genes described by Marshall et al., Theor. Appl. Genet. 83: 435 (1992).

(C) A herbicide inhibiting photosynthesis such as triazines (psbA and gs+genes) and benzonitriles (nitrilase gene). Przibilla et al., Plant Cell 3: 169 (1991) (transformation of Chlamydomonas using plasmids encoding mutant psbA genes); U.S. Pat. 4,810,648 to Stalker (nucleotide sequences for nitrilase genes, available under ATCC Accession Nos. 53435, 67441 and 67442); Hayes et al., Biochem. J. 285:173 (1992) (cloning and expression of DNA coding for glutathione S-transferase).

3. Genes Conferring, Or Contributing To, Value-Added Traits in Maize (A) Modified fatty acid metabolism, for example, transforming a plant with an antisense gene of stearoyl-ACP desaturase to increase stearic acid content. See, e.g., Knultzon et al., Proc. Natl. Acad. Sci. USA 89: 2624 (1992).

(B) Decreased phytate content
  (1) Phytase-encoding genes enhancing breakdown of phytate by adding free phosphate to the transformed plant. See, e.g., Van Hartingsveldt et al., Gene 127: 87 (1993) (nucleotide sequence of an *Aspergillus niger* phytase gene).
  (2) Genes reducing phytate content. For example, cloning, then reintroducing DNA associated with the allele responsible for maize mutants characterized by low levels of phytic acid. See, e.g., Raboy et al., Maydica 35: 383 (1990).

(C) Modified carbohydrate compositions. For example, transforming plants with a gene encoding an enzyme altering starch branching patterns. See, e.g., Shiroza et al., J. Bacteriol. 170: 810 (1988) (nucleotide sequence of *Streptococcus mutans* fructosyltransferase gene); Steinmetz et al., Mol. Gen. Genet. 200: 220 (1985) (nucleotide sequence of *Bacillus subtilis* levansucrase gene); Pen et al., Bio/Technology 10: 292 (1992) (production of transgenic plants expressing *Bacillus licheniformis* α-amylase); Elliot et al., Plant Molec. Biol. 21: 515 (1993) (nucleotide sequences of tomato invertase genes); Sogaard et al., J. Biol. Chem. 268: 22480 (1993) (site-directed mutagenesis of barley α-amylase gene); and Fisher et al., Plant Physiol. 102: 1045 (1993) (maize endosperm starch branching enzyme II).

Maize Transformation Methods

Plant transformation methods contemplated to transform the hybrid of this invention include biological and physical plant transformation protocols. See, e.g., Miki et al., "Procedures for Introducing Foreign DNA into Plants" IN Methods in Plant Molecular Biology and Biotechnology, B. R. Glick and J. E. Thompson, Eds. (CRC Press, Inc., Boca Raton, 1993) pages 67–88; Gruber et al., "Vectors for Plant Transformation" in Methods in Plant Molecular Biology and Biotechnology (expression vectors and in vitro culture methods for plant cell or tissue transformation and regeneration of plants); and B. R. Glick and J. E. Thompson, Eds., CRC Press, Inc., Boca Raton, (1993) pages 89–119 (expression vectors and in vitro culture methods for plant cell or tissue transformation and regeneration of plants).

A. Agrobacterium-mediated Transformation

One method for introducing an expression vector into plants is based on the natural transformation system of Agrobacterium. See, e.g., Horsch et al., Science 227: 1229 (1985). *A. tumefaciens* and *A. rhizogenes* are plant pathogenic soil bacteria which infect plant cells and genetically transform plant cells during infection. The Ti and Ri plasmids of *A. tumefaciens* and *A. rhizogenes*, respectively, carry genes responsible for genetic transformation of the plant. See, e.g., Kado, Crit. Rev. Plant. Sci.10: 1 (1991). Descriptions of Agrobacterium vector systems and methods for Agrobacterium-mediated gene transfer (transformation) are provided by Gruber et al., "Vectors for Plant Transformation" IN Methods in Plant Molecular Biology and Biotechnology; Miki et al., "Procedures for Introducing Foreign DNA into Plants" IN Methods in Plant Molecular Biology and Biotechnology, B. R. Glick and J. E. Thompson, Eds. (CRC Press, Inc., Boca Raton, 1993) pages 67–88; and Moloney et al., Plant Cell Reports 8: 238 (1989); and U.S. Pat. No. 5,591,616 to Hiei et al.

B. Direct Gene Transfer

Despite the fact that the host range for Agrobacterium-mediated transformation is broad and with some exceptions in rice and maize, most major cereal crop species and gymnosperms have generally been recalcitrant to this mode of gene transfer. Hiei et al., The Plant Journal 6: 271–282 (1994); and U.S. Pat. No. 5,591,616 to Hiei et al. Several methods of plant transformation, collectively referred to as direct gene transfer, have been developed as alternatives to Agrobacterium-mediated transformation.

One generally applicable method of plant transformation is microprojectile-mediated transformation, wherein an expression vector is applied to the surfaces of 1 to 4 $\mu$m diameter microprojectiles. The expression vector is then introduced into plant tissues with a biolistic device which accelerates the microprojectiles to velocities sufficient to penetrate plant cell walls and membranes of the tissues, e.g., 300 to 600 m/s. Sanford et al., Part. Sci. Technol. 5: 27 (1987); Sanford, Trends Biotech. 6: 299 (1988); Klein et al., Bio/Technology 6: 559–563 (1988); Sanford, Physiol Plant 79: 206 (1990); Klein et al., Biotechnology 10: 268 (1992); U.S. Pat. No. 5,550,318 to Adams et al.; U.S. Pat. No. 5,887,023 to Sautter et al; and U.S. Pat. Nos. 5,886,244 and 5,990,387 to Tomes et al., the contents of each hereby incorporated by reference. In maize, several target tissues can be bombarded with DNA-coated microprojectiles to produce transgenic, hence derived, plants, including, for example, callus (Type I or Type II), immature embryos, and meristematic tissue.

Another method for physical delivery of DNA to plants is sonication of target cells. Zhang et al., Bio/Technology 9: 996 (1991). Alternatively, liposome or spheroplast fusion may be used to introduce expression vectors into plants. Deshayes et al., EMBO J., 4: 2731 (1985); Christou et al., Proc Natl. Acad. Sci. U.S.A. 84: 3962 (1987). Direct uptake of DNA into protoplasts using $CaCl_2$ precipitation, polyvinyl alcohol or poly-L-ornithine has also been reported. Hain et al., Mol. Gen. Genet. 199: 161 (1985) and Draper et al., Plant Cell Physiol. 23: 451 (1982). Electroporation of protoplasts and whole cells and tissues has also been described. Donn et al., In Abstracts of VIIth International Congress on Plant Cell and Tissue Culture IAPTC, A2-38, p 53 (1990); D'Halluin et al., Plant Cell 4: 1495–1505 (1992); Spencer et al., Plant Mol. Biol. 24: 51–61(1994); and U.S. Pat. No. 5,384,263 to Krzyzek et al., previously referenced.

Following transformation of maize target tissues, expression of the above-described selectable marker genes allows for preferential selection of transformed cells, tissues and/or plants using regeneration and selection methods known to the art.

The foregoing transformation methods may be used to produce transgenic derived maize hybrids of this invention. These transgenic maize hybrids may then be selfed or crossed with another (non-transformed or transformed) inbred line to produce a segregating generation of transgenic individuals for developing improved inbred lines.

Industrial Applicability

Maize is used as human food, livestock feed, and as raw materials in industry. The food uses of maize, in addition to human consumption of maize kernels, include products of the dry-milling and wet-milling industries. The principal products of maize dry milling are grits, meal and flour. The maize wet-milling industry provides maize starch, maize syrup, and dextrose for food use. Maize oil is recovered from maize germ which is a by-product of both the dry-milling and wet-milling industries.

Maize, including both grain and non-grain portions of the plant, is also used extensively as livestock feed, primarily for beef cattle, dairy cattle, swine, and poultry.

Industrial uses of maize include production of ethanol, maize starch in the wet-milling industry, and maize flour in the dry-milling industry. The industrial applications of maize starch and flour are based on functional properties such as viscosity, film formation, adhesive properties, and abilities to suspend particles. Maize starch and flour have applications in paper and textile industries. Other industrial uses include adhesives, building materials, foundry binders, laundry starches, explosives, oil-well muds, and mining applications.

Plant parts other than the grain of maize are also used in industry. For example, stalks and husks are made into paper and wallboard and cobs are used for fuel and in making charcoal.

Hence, the seed of maize hybrid RPG824, the hybrid maize plant, various parts of the hybrid maize plant, and transgenic versions of the foregoing, can be utilized for human food, livestock feed, and as a raw material in industry.

Deposits

Applicant has made a deposit of at least 2500 seeds of maize hybrid RPG824 with the American Type Culture Collection (ATCC), Manassas, Va. 20110 USA, ATCC Deposit No. PTA-4729. The seeds deposited with the ATCC on Sep. 27, 2002 were obtained from the Applicant and maintained by Applicant's attorney since prior to the filing date of this application. This seed deposit of maize hybrid RPG824 will be maintained in the ATCC depository, which is a public depository, for a period of 30 years, or five years after the most recent request, or for the effective life of the patent, whichever is longer, and will be replaced if it becomes nonviable during that period. Additionally, Applicant has satisfied all the requirements of 37 C.F.R. §§.1.801–1.809, including providing an indication of the viability of the sample. Applicant imposes no restrictions on the availability of the deposited material from the ATCC; however, Applicant has no authority to waive any restrictions imposed by law on the transfer of biological material or its transportation in commerce. Applicant does not waive any infringement of rights granted under this patent.

The foregoing invention has been described in detail by way of illustration and example for purposes of clarity and understanding. However, it will be obvious that certain changes and modifications such as single gene modifications and mutations, somaclonal variants, variant individuals selected from large populations of the plants of the instant inbred and the like may be practiced within the scope of the invention as limited only by the scope of the appended claims.

What is claimed is:

1. A seed of a maize hybrid designated RPG824, a representative sample of said seed deposited under ATCC Accession No. PTA-4729.

2. A regenerable cell arising from the seed of claim 1.

3. A tissue culture arising from culturing the regenerable cell of claim 2 and capable of regenerating plants capable of expressing all the morphological and physiological characteristics of the maize hybrid RPG824.

4. A maize plant arising from regenerating the tissue culture of claim 3 and capable of expressing all the morphological and physiological characteristics of the maize hybrid RPG824.

5. A maize plant arising from the seed of claim 1 and having all the physiological and morphological characteristics of maize hybrid RPG824.

6. Pollen arising from the maize plant of claim 5.

7. An ovule arising from the maize plant of claim 5.

8. A regenerable cell arising from the maize plant of claim 5.

9. A tissue culture of regenerable cells or protoplasts cultured from maize hybrid RPG824, representative seed deposited under ATCC Accession No. PTA-4729, the tissue culture capable of regenerating plants capable of expressing all the morphological and physiological characteristics of the maize hybrid RPG824.

10. A tissue culture according to claim 9, the cells or protoplasts arising from an explanted tissue selected from the group consisting of a leaf, a pollen grain, an embryo, a root, a root tip, an anther, a silk, a flower, a seed, an ear, a cob, a husk, and a stalk.

11. A process of producing a somoclonal maize variant, comprising:

culturing the tissue culture of claim 9; and regenerating plants from said tissue culture, at least one of said regenerated plants a somoclonal variant.

12. A maize plant regenerated from the tissue culture of claim 9, the maize plant capable of expressing all the morphological and physiological characteristics of maize hybrid RPG824.

13. A process for producing a hybrid maize seed, the maize hybrid seed designated as RPG824, a representative seed sample deposited under ATCC Accession No. PTA-4729, the process comprising crossing a first maize plant with a second maize plant such that a seed develops, said first maize plant being RPK7250 and said second maize plant being RPK7346, a representative seed sample of RPK7250 deposited under ATCC Accession No. PTA-4730, and a representative seed sample of RPK7346 deposited under ATCC Accession No. PTO-4731.

14. A zygote arising from the process of claim 13.

15. The process of claim 13, further comprising harvesting the seed.

16. The seed arising from the process of claim 13.

17. A maize plant, or parts thereof, arising from the seed of claim 16.

18. The process of claim 13, further comprising detasseling one of said first and said second plants.

19. The process of claim 13, further comprising planting the seeds of said first and second plants in proximity such that the first plant is fertilized by pollen from the second plant.

20. A process of producing a maize seed, comprising:
   identifying an inbred maize plant, said inbred maize plant disposed within an assemblage of hybrid maize plants arising from the seed of claim 1, said inbred maize plant designated as RPK7250 or RPK7346, a representative sample of RPK7250 deposited under ATCC Accession No. PTA-4730 and a representative sample of RPK7346 deposited under ATCC Accession No. PTA-4730; and
   pollinating the inbred maize plant.

21. The process of claim 20, in which the inbred maize plant is self-pollinated.

22. The process of claim 20, in which the inbred maize plant is pollinated with pollen from another maize plant, the other maize plant not arising from the seed of claim 1.

23. The process of claim 20, in which identifying the inbred maize plant comprises identifying a plant with decreased vigor.

24. The process of claim 20, in which identifying the inbred maize plant comprises identifying a seed or a plant with a homozygous genotype.

25. The process of claim 20, in which the inbred maize plant is pollinated in a manner preserving the homozygosity of the inbred maize plant.

26. A zygote arising from the process of claim 20.

27. A maize seed arising from the process of claim 20.

28. A maize plant arising from the maize seed of claim 27.

29. A process of inbreeding a maize plant, the process comprising a protocol selected from the group consisting of inbreeding a maize plant arising from the seed of claim 1 such that seed arises therefrom; and crossing the maize plant arising from the seed of claim 1 with another maize plant such that seed arises therefrom, then inbreeding a plant arising from the seed from the cross.

30. The process of claim 29, further comprising harvesting the seed.

31. The process of claim 30, further comprising:
   planting the seed obtained from claim 30 such that maize plants arise therefrom;
   inbreeding the maize plants such that seed arise therefrom; and
   harvesting the seed arising from said inbreeding,
   said planting, inbreeding, and harvesting cyclically continuing until a family obtained from a plant arising from at least one of said seed is substantially homogeneous.

32. The process of claim 31, further comprising transforming at least one of said maize plants arising from said inbreeding.

33. A zygote obtained from the process of claim 29.

34. A seed obtained from the process of claim 29.

35. A plant arising from the seed of claim 34.

36. The process of claim 29, in which inbreeding comprises self-pollination.

37. The process of claim 29, in which inbreeding comprises sibbing.

38. A process of producing maize grain, comprising:
   providing the hybrid maize seed of claim 1; and
   planting the hybrid maize seed such that hybrid maize plants grow therefrom and such that grain arises from said hybrid maize plants, said maize plants capable of expressing all the morphological and physiological characteristics of the maize hybrid RPG824.

39. The process of claim 38, further comprising harvesting the grain.

40. The grain of claim 38.

* * * * *